(12) United States Patent
Arkenau-Marić et al.

(10) Patent No.: US 8,722,086 B2
(45) Date of Patent: May 13, 2014

(54) DOSAGE FORM WITH IMPEDED ABUSE

(75) Inventors: Elisabeth Arkenau-Marić, Köln (DE); Johannes Bartholomaeus, Aachen (DE); Iris Ziegler, Neusäβ (DE); Marcel Haupts, Stolberg (DE)

(73) Assignee: Gruenenthal GmbH, Aachen (DE)

( * ) Notice: Subject to any disclaimer, the term of this patent is extended or adjusted under 35 U.S.C. 154(b) by 669 days.

(21) Appl. No.: 12/044,586

(22) Filed: Mar. 7, 2008

(65) Prior Publication Data
US 2009/0004267 A1   Jan. 1, 2009

(30) Foreign Application Priority Data
Mar. 7, 2007   (DE) .......................... 10 2007 011 485

(51) Int. Cl.
*A61K 9/20* (2006.01)
*A61K 9/50* (2006.01)
*A61K 9/16* (2006.01)

(52) U.S. Cl.
CPC ............. *A61K 9/1635* (2013.01); *A61K 9/1652* (2013.01); *A61K 9/1641* (2013.01)
USPC .......................................... 424/465; 424/501

(58) Field of Classification Search
None
See application file for complete search history.

(56) References Cited

U.S. PATENT DOCUMENTS

| | | |
|---|---|---|
| 2,524,855 A | 10/1950 | Schnider et al. |
| 2,806,033 A | 9/1957 | Lewenstein et al. |
| 2,987,445 A | 6/1961 | Levesque |
| 3,652,589 A | 3/1972 | Flick et al. |
| 3,806,603 A | 4/1974 | Gaunt et al. |
| 3,865,108 A | 2/1975 | Hartop |
| 3,966,747 A | 6/1976 | Monkovic et al. |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. |
| 4,070,497 A | 1/1978 | Wismer et al. |
| 4,175,119 A | 11/1979 | Porter |
| 4,200,704 A | 4/1980 | Stanley et al. |
| 4,207,893 A | 6/1980 | Michaels |
| 4,262,017 A | 4/1981 | Kuipers |
| 4,343,789 A | 8/1982 | Kawata et al. |
| 4,353,887 A | 10/1982 | Hess |
| 4,404,183 A | 9/1983 | Kawata et al. |
| 4,427,681 A | 1/1984 | Manshi |
| 4,427,778 A | 1/1984 | Zabriskie |
| 4,457,933 A | 7/1984 | Gordon et al. |
| 4,462,941 A | 7/1984 | Lee et al. |
| 4,473,640 A | 9/1984 | Combie et al. |
| 4,483,847 A | 11/1984 | Augart |
| 4,603,143 A | 7/1986 | Schmidt |
| 4,612,008 A | 9/1986 | Wong et al. |
| 4,629,621 A | 12/1986 | Snipes |
| 4,667,013 A | 5/1987 | Reichle |
| 4,690,822 A | 9/1987 | Uemura et al. |
| 4,713,243 A | 12/1987 | Schiraldi et al. |
| 4,744,976 A | 5/1988 | Snipes et al. |
| 4,764,378 A | 8/1988 | Keitn et al. |
| 4,765,989 A | 8/1988 | Wong et al. |
| 4,774,074 A | 9/1988 | Snipes |
| 4,774,092 A | 9/1988 | Hamilton |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk |
| 4,940,556 A | 7/1990 | MacFarlane et al. |
| 4,957,668 A | 9/1990 | Plackard et al. |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinity et al. |
| 5,073,379 A | 12/1991 | Klimesch et al. |
| 5,082,668 A | 1/1992 | Wong et al. |

(Continued)

FOREIGN PATENT DOCUMENTS

| AR | 046994 A1 | 12/2004 |
|---|---|---|
| AR | 045353 A1 | 10/2005 |

(Continued)

OTHER PUBLICATIONS

International Search Report and Written Opinion issued by the European Patent Office for PCT/EP2008/001672 on Mar. 3, 2008.
Jan. 6, 2011 Letter from Dr. Rick Matos, Ph.D.
Dachille, F. et al., "High-Pressure Phase Transformation in Laboratory Mechanical Mixers and Mortars", 1960., Nature, 186, pp. 1-2 (abstract).
Maggi, L. et al., "High molecular weight polyethylene oxides (PEOs) as an alternative to HPMC in controlled release dosage form", 2000, International Journal of Pharmaceutics, 195 pp. 229-238.
Freed et al. pH control of nucleophilic/electrophilic oxidation. International Journal of Pharmaceutics. 2008, vol. 357, pp. 180-188.
Waterman et al. Stabilization of Pharmaceuticals to Oxidative Degradation. Pharmaceutical Development and Technology. 2002, vol. 7, No. 1, pp. 1-32.
Handbuch der Kunststoff-Extrusionstechnik 1, "Grundlagen" in Chapter 1.2 "Klassifizierung von Extrudern", pp. 3-7. 1989.
2.9 Methoden der pharmazeutischen Technologie 143-144, 1997.

(Continued)

*Primary Examiner* — Brian Gulledge
(74) *Attorney, Agent, or Firm* — Norris McLauglin & Marcus, P.A.

(57) ABSTRACT

A multiparticulate dosage form formulated to make misuse more difficult containing least one active substance with potential for misuse (A), at least one synthetic or natural polymer (C), optionally at least one natural, semi-synthetic or synthetic wax (D), at least one disintegrant (E) and optionally one or more additional physiologically compatible excipients (B), wherein the individual particles of the dosage form display a breaking strength of at least 500 N and a release of active substance of at least 75% after 45 minutes measured according to Ph.Eur. in the paddle mixer with sinker in 600 ml of aqueous buffer solution with a pH value of 1.2 at 37° C. and 75 rpm.

25 Claims, 2 Drawing Sheets

(56) References Cited

U.S. PATENT DOCUMENTS

| | | |
|---|---|---|
| 5,126,151 A | 6/1992 | Bodor et al. |
| 5,139,790 A | 8/1992 | Snipes |
| 5,145,944 A | 9/1992 | Steinmann |
| 5,149,538 A | 9/1992 | Granger et al. |
| 5,169,645 A | 12/1992 | Shukla et al. |
| 5,190,760 A | 3/1993 | Baker |
| 5,198,226 A | 3/1993 | MacFarlane et al. |
| 5,200,197 A | 4/1993 | Wright et al. |
| 5,211,892 A | 5/1993 | Gueret |
| 5,225,417 A | 7/1993 | Dappen |
| 5,273,758 A | 12/1993 | Royce |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludgwig et al. |
| RE34,990 E | 7/1995 | Khanna et al. |
| 5,458,887 A | 10/1995 | Chen et al. |
| 5,460,826 A | 10/1995 | Merrill et al. |
| 5,472,943 A | 12/1995 | Crain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,593,694 A | 1/1997 | Hayashida et al. |
| 5,601,842 A | 2/1997 | Bartholomaeus |
| 5,620,697 A | 4/1997 | Tormala et al. |
| 5,681,517 A | 10/1997 | Metzger |
| 5,707,636 A | 1/1998 | Rodriguez et al. |
| 5,741,519 A | 4/1998 | Rosenberg et al. |
| 5,792,474 A | 8/1998 | Rauchfuss |
| 5,801,201 A | 9/1998 | Graudums et al. |
| 5,811,126 A | 9/1998 | Krisnamurthy |
| 5,849,240 A | 12/1998 | Miller et al. |
| 5,866,164 A | 2/1999 | Kuczynski et al. |
| 5,908,850 A | 6/1999 | Zeitlin et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merill et al. |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,071,970 A | 6/2000 | Mueller et al. |
| 6,077,538 A | 6/2000 | Merrill et al. |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,228,863 B1 | 5/2001 | Palermo et al. |
| 6,235,825 B1 | 5/2001 | Yoshida et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,326,027 B1 | 12/2001 | Miller et al. |
| 6,340,475 B2 | 1/2002 | Shell et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko et al. |
| 6,375,963 B1 | 4/2002 | Repka et al. |
| 6,399,100 B1 | 6/2002 | Clancy et al. |
| 6,419,954 B1 | 7/2002 | Chu et al. |
| 6,436,441 B1 | 8/2002 | Sako et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breithenbach et al. |
| 6,562,375 B1 | 5/2003 | Sako et al. |
| 6,569,506 B1 | 5/2003 | Jerdee et al. |
| 6,572,889 B1 | 6/2003 | Guo |
| 6,592,901 B2 | 7/2003 | Durig et al. |
| 6,623,754 B2 | 9/2003 | Guo et al. |
| 6,635,280 B2 | 10/2003 | Shell et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastloll et al. |
| RE39,593 E | 4/2007 | Buschmann et al. |
| 7,201,920 B2 | 4/2007 | Kumar et al. |
| 7,214,385 B2 | 5/2007 | Gruber |
| 7,300,668 B2 | 11/2007 | Pryce et al. |
| 7,388,068 B2 | 6/2008 | Falk et al. |
| 7,399,488 B2 | 7/2008 | Hirsh et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomäus et al. |
| 7,851,482 B2 | 12/2010 | Dung et al. |
| 7,939,543 B2 | 5/2011 | Kupper |
| 7,994,364 B2 | 8/2011 | Fischer et al. |
| 8,075,872 B2 | 12/2011 | Arkenau-Maric et al. |
| 8,101,630 B2 | 1/2012 | Kumar et al. |
| 8,114,383 B2 | 2/2012 | Bartholomaus et al. |
| 8,114,384 B2 | 2/2012 | Arkenau et al. |
| 8,114,838 B2 | 2/2012 | Marchionni |
| 8,192,722 B2 | 6/2012 | Arkenau-Maric et al. |
| 8,309,060 B2 | 11/2012 | Bartholomaus et al. |
| 8,309,122 B2 | 11/2012 | Kao et al. |
| 8,323,889 B2 | 12/2012 | Arkenau-Maric et al. |
| 8,329,216 B2 | 12/2012 | Kao et al. |
| 8,337,888 B2 | 12/2012 | Wright et al. |
| 8,383,152 B2 | 2/2013 | Jans et al. |
| 8,420,056 B2 | 4/2013 | Arkenau-Maric et al. |
| 8,445,023 B2 | 5/2013 | Guimberteau et al. |
| 2001/0038852 A1 | 11/2001 | Kolter et al. |
| 2002/0001270 A1 | 1/2002 | Fukuchi et al. |
| 2002/0015730 A1 | 2/2002 | Hoffmann et al. |
| 2002/0018719 A1 | 2/2002 | Arilla et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0176888 A1 | 11/2002 | Bartholomaeus et al. |
| 2002/0192277 A1 | 12/2002 | Oshlack et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0031546 A1 | 2/2003 | Araki et al. |
| 2003/0044458 A1 | 3/2003 | Wright et al. |
| 2003/0044464 A1 | 3/2003 | Zeigler et al. |
| 2003/0064099 A1 | 4/2003 | Oshlack et al. |
| 2003/0068276 A1 | 4/2003 | Hughes et al. |
| 2003/0068370 A1 | 4/2003 | Sackler |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0077297 A1 | 4/2003 | Chen et al. |
| 2003/0091630 A1 | 5/2003 | Louie-Helm et al. |
| 2003/0104052 A1 | 6/2003 | Berner et al. |
| 2003/0104053 A1 | 6/2003 | Gusler et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |

(56) References Cited

U.S. PATENT DOCUMENTS

| | | |
|---|---|---|
| 2003/0129230 A1 | 7/2003 | Baichwal et al. |
| 2003/0133985 A1 | 7/2003 | Louie-Helm et al. |
| 2003/0152622 A1 | 8/2003 | Louie-Helm et al. |
| 2003/0158242 A1 | 8/2003 | Kugelmann |
| 2003/0175326 A1 | 9/2003 | Thombre |
| 2003/0198677 A1 | 10/2003 | Pryce Lewis et al. |
| 2003/0215508 A1 | 11/2003 | Davis et al. |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack |
| 2004/0091528 A1 | 5/2004 | Rogers et al. |
| 2004/0126428 A1 | 7/2004 | Hughes et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0185105 A1 | 9/2004 | Berner et al. |
| 2004/0213845 A1 | 10/2004 | Sugihara |
| 2004/0213848 A1 | 10/2004 | Li et al. |
| 2005/0015730 A1 | 1/2005 | Gunturi et al. |
| 2005/0031546 A1 | 2/2005 | Bartholomaus et al. |
| 2005/0058706 A1 | 3/2005 | Bartholomaeus et al. |
| 2005/0063214 A1 | 3/2005 | Takashima |
| 2005/0089475 A1 | 4/2005 | Gruber |
| 2005/0095291 A1 | 5/2005 | Oshlack et al. |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaeus et al. |
| 2005/0186139 A1 | 8/2005 | Bartholomaeus et al. |
| 2005/0191244 A1 | 9/2005 | Bartholomaus |
| 2005/0191340 A1 | 9/2005 | Bartholomaeus et al. |
| 2005/0192333 A1 | 9/2005 | Hinze et al. |
| 2005/0214223 A1 | 9/2005 | Bartholomaeus et al. |
| 2005/0222188 A1 | 10/2005 | Chapman et al. |
| 2005/0236741 A1 | 10/2005 | Arkenau et al. |
| 2005/0245556 A1 | 11/2005 | Brogman et al. |
| 2005/0266084 A1 | 12/2005 | Li et al. |
| 2006/0002859 A1 | 1/2006 | Arkenau et al. |
| 2006/0002860 A1* | 1/2006 | Bartholomaus et al. ..... 424/10.1 |
| 2006/0004034 A1 | 1/2006 | Hinze et al. |
| 2006/0009478 A1 | 1/2006 | Friedmann et al. |
| 2006/0039864 A1 | 2/2006 | Bartholomaeus et al. |
| 2006/0099250 A1* | 5/2006 | Tian et al. .................... 424/464 |
| 2006/0104909 A1 | 5/2006 | Vaghefi |
| 2006/0182801 A1 | 8/2006 | Breder et al. |
| 2006/0188447 A1 | 8/2006 | Arkenau-Maric et al. |
| 2006/0193782 A1 | 8/2006 | Bartholomaus et al. |
| 2006/0193914 A1 | 8/2006 | Arkenau et al. |
| 2006/0240110 A1 | 10/2006 | Kiick et al. |
| 2006/0269603 A1 | 11/2006 | Brown Miller et al. |
| 2007/0003616 A1 | 1/2007 | Arkenau-Maric et al. |
| 2007/0020188 A1* | 1/2007 | Sackler ........................ 424/10.2 |
| 2007/0020335 A1 | 1/2007 | Chen et al. |
| 2007/0048228 A1 | 3/2007 | Arkenau-Maric et al. |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |
| 2007/0190142 A1 | 8/2007 | Breitenbach et al. |
| 2007/0196396 A1 | 8/2007 | Pilgaonkar et al. |
| 2007/0196481 A1 | 8/2007 | Amidon et al. |
| 2007/0224129 A1 | 9/2007 | Guimberteau et al. |
| 2007/0231268 A1 | 10/2007 | Emigh et al. |
| 2007/0264327 A1 | 11/2007 | Kumar et al. |
| 2007/0269505 A1 | 11/2007 | Flath et al. |
| 2008/0069871 A1 | 3/2008 | Vaughn et al. |
| 2008/0081290 A1 | 4/2008 | Wada et al. |
| 2008/0220079 A1 | 9/2008 | Chen |
| 2008/0234352 A1 | 9/2008 | Fischer et al. |
| 2008/0247959 A1 | 10/2008 | Bartholomaus et al. |
| 2008/0248113 A1 | 10/2008 | Bartholomaus et al. |
| 2008/0311049 A1 | 12/2008 | Bartholomaus et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0312264 A1 | 12/2008 | Arkenau-Maric et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0017121 A1 | 1/2009 | Berner et al. |
| 2009/0081287 A1 | 3/2009 | Wright et al. |
| 2009/0081290 A1 | 3/2009 | McKenna et al. |
| 2009/0117191 A1 | 5/2009 | Brown Miller et al. |
| 2009/0202634 A1 | 8/2009 | Jans et al. |
| 2009/0317355 A1 | 12/2009 | Roth et al. |
| 2010/0015223 A1 | 1/2010 | Cailly-Deufestel et al. |
| 2010/0092553 A1 | 4/2010 | Guimberteau et al. |
| 2010/0098758 A1 | 4/2010 | Bartholomaus et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Anderson et al. |
| 2010/0221322 A1 | 9/2010 | Bartholomaus et al. |
| 2010/0249045 A1 | 9/2010 | Babul |
| 2010/0260833 A1 | 10/2010 | Bartholomaus et al. |
| 2010/0280047 A1 | 11/2010 | Kolter et al. |
| 2011/0020451 A1 | 1/2011 | Bartholomaus et al. |
| 2011/0020454 A1 | 1/2011 | Lamarca Casado |
| 2011/0038930 A1 | 2/2011 | Barnscheid et al. |
| 2011/0082214 A1 | 4/2011 | Fauer et al. |
| 2011/0097404 A1 | 4/2011 | Oshlack et al. |
| 2011/0159100 A1 | 6/2011 | Anderson et al. |
| 2011/0187017 A1 | 8/2011 | Haupts |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0107250 A1 | 5/2012 | Bartholomaeus et al. |
| 2012/0108622 A1 | 5/2012 | Wright et al. |
| 2012/0135071 A1 | 5/2012 | Bartholomaeus et al. |
| 2012/0136021 A1 | 5/2012 | Barnscheid et al. |
| 2013/0028970 A1 | 1/2013 | Schwier et al. |
| 2013/0129826 A1 | 5/2013 | Geiler et al. |
| 2013/0225625 A1 | 8/2013 | Barnscheid et al. |

FOREIGN PATENT DOCUMENTS

| | | |
|---|---|---|
| AR | 049562 A1 | 8/2006 |
| AR | 053304 A1 | 5/2007 |
| AR | 054222 A1 | 6/2007 |
| AR | 054328 A1 | 6/2007 |
| AU | 2003237944 | 12/2003 |
| AU | 2003274071 | 5/2004 |
| AU | 2003278133 | 5/2004 |
| AU | 2003279317 | 5/2004 |
| AU | 2004264666 | 2/2005 |
| AU | 2004264667 | 2/2005 |
| AU | 2004308653 | 4/2005 |
| AU | 2005259476 | 1/2006 |
| AU | 2005259478 | 1/2006 |
| AU | 2006/210145 B2 | 8/2006 |
| AU | 2006210145 | 8/2006 |
| AU | 2009207796 | 7/2009 |
| AU | 2009243681 | 11/2009 |
| BR | P10413318 | 10/2006 |
| BR | P10413361 | 10/2006 |
| BR | P10513300 | 5/2008 |
| BR | P10606145 | 2/2009 |
| CA | 722109 A | 11/1965 |
| CA | 2082573 | 5/1993 |
| CA | 2577233 A1 | 10/1997 |
| CA | 2650637 A1 | 10/1997 |
| CA | 2 317 747 A1 | 7/1999 |
| CA | 2352874 | 6/2000 |
| CA | 2456322 A1 | 2/2003 |
| CA | 2502965 | 5/2004 |
| CA | 2534925 | 2/2005 |
| CA | 2534932 | 2/2005 |
| CA | 2551231 | 7/2005 |
| CA | 2572352 | 1/2006 |
| CA | 2572491 | 1/2006 |
| CA | 2595954 | 7/2006 |

(56) References Cited

FOREIGN PATENT DOCUMENTS

| | | |
|---|---|---|
| CA | 2229650 C | 8/2006 |
| CA | 2594713 A1 | 8/2006 |
| CA | 2595979 | 8/2006 |
| CA | 2625055 A1 | 4/2007 |
| CA | 2713128 | 7/2009 |
| CA | 2723438 | 11/2009 |
| CA | 2595954 C | 1/2011 |
| CH | 689109 | 10/1998 |
| CL | 20162004 | 5/2005 |
| CL | 20172004 A1 | 5/2005 |
| CL | 200403308 A1 | 9/2005 |
| CL | 200500952 | 11/2005 |
| CL | 200501624 | 12/2005 |
| CL | 200501625 | 6/2006 |
| CN | 87102755 A | 10/1987 |
| CN | 1980643 | 4/2005 |
| CN | 101010071 | 6/2005 |
| CN | 1671475 A | 9/2005 |
| CN | 101022787 | 1/2006 |
| CN | 001863513 | 11/2006 |
| CN | 001863514 | 11/2006 |
| CN | 01917862 | 2/2007 |
| CN | 101011395 A | 8/2007 |
| CN | 101027044 | 8/2007 |
| CN | 101057849 A | 10/2007 |
| CN | 101111232 | 1/2008 |
| CN | 101175482 | 2/2008 |
| DE | 2530563 | 1/1977 |
| DE | 4229085 | 3/1994 |
| DE | 43 09 528 A1 | 9/1994 |
| DE | 4446470 | 6/1996 |
| DE | 69400215 | 10/1996 |
| DE | 19522899 C1 | 12/1996 |
| DE | 2808505 | 1/1997 |
| DE | 197 53 534 A1 | 6/1999 |
| DE | 198 00 698 A1 | 7/1999 |
| DE | 19800689 C1 | 7/1999 |
| DE | 198 22 979 A1 | 12/1999 |
| DE | 69229881 | 12/1999 |
| DE | 19855440 | 6/2000 |
| DE | 19856147 | 6/2000 |
| DE | 19940740 | 3/2001 |
| DE | 19960494 | 6/2001 |
| DE | 10036400 | 6/2002 |
| DE | 10036400 A1 | 6/2002 |
| DE | 69429710 | 8/2002 |
| DE | 10250083 | 12/2003 |
| DE | 10250084 | 5/2004 |
| DE | 10250087 | 5/2004 |
| DE | 10250088 | 5/2004 |
| DE | 103 36 400 A1 | 3/2005 |
| DE | 10336400 A1 | 3/2005 |
| DE | 10 361 596 | 9/2005 |
| DE | 10 2004 020 220 | 11/2005 |
| DE | 102004019916 | 11/2005 |
| DE | 102004020220 | 11/2005 |
| DE | 10 2004 032 049 A1 | 1/2006 |
| DE | 10 2004 032 103 A1 | 1/2006 |
| DE | 102004032051 A1 | 1/2006 |
| DE | 10 2005 005 449 | 8/2006 |
| DE | 102005005446 A1 | 8/2006 |
| DE | 102007011485 | 9/2008 |
| DK | 1658055 | 7/2007 |
| DK | 1658054 | 10/2007 |
| DK | 1515702 | 1/2009 |
| EC | SP066345 | 8/2006 |
| EP | 0008131 | 2/1980 |
| EP | 0216453 | 2/1980 |
| EP | 0043254 A1 | 1/1982 |
| EP | 0008131 B1 | 12/1982 |
| EP | 0177893 | 4/1986 |
| EP | 0216453 A2 | 4/1987 |
| EP | 0226061 | 6/1987 |
| EP | 0228417 | 7/1987 |
| EP | 0229652 A2 | 7/1987 |
| EP | 0232877 | 8/1987 |
| EP | 0240906 A2 | 10/1987 |
| EP | 0261616 A2 | 3/1988 |
| EP | 0270954 | 6/1988 |
| EP | 0277289 | 8/1988 |
| EP | 0293066 | 11/1988 |
| EP | 0261616 A3 | 2/1989 |
| EP | 0328775 | 8/1989 |
| EP | 0228417 B1 | 8/1990 |
| EP | 0229652 B1 | 10/1991 |
| EP | 0477135 A1 | 3/1992 |
| EP | 0277289 B1 | 4/1992 |
| EP | 0293066 B1 | 4/1993 |
| EP | 0270954 B1 | 5/1993 |
| EP | 0544144 A1 | 6/1993 |
| EP | 0583726 | 2/1994 |
| EP | 0598606 | 5/1994 |
| EP | 0636370 A1 | 2/1995 |
| EP | 0641195 A1 | 3/1995 |
| EP | 0647448 A1 | 4/1995 |
| EP | 0654263 A1 | 5/1995 |
| EP | 0661045 | 7/1995 |
| EP | 0675710 A1 | 10/1995 |
| EP | 0682945 | 11/1995 |
| EP | 0 693 475 B1 | 1/1996 |
| EP | 0696598 | 2/1996 |
| EP | 0583726 B1 | 11/1996 |
| EP | 0756480 A1 | 2/1997 |
| EP | 0760654 A1 | 3/1997 |
| EP | 0 780 369 B1 | 6/1997 |
| EP | 0785775 A1 | 7/1997 |
| EP | 0 761 211 A1 | 12/1997 |
| EP | 0809488 A1 | 12/1997 |
| EP | 0 820 693 A1 | 1/1998 |
| EP | 0820698 | 1/1998 |
| EP | 0857062 A2 | 8/1998 |
| EP | 0864324 A1 | 9/1998 |
| EP | 0864326 A2 | 9/1998 |
| EP | 0598606 B1 | 6/1999 |
| EP | 0675710 B1 | 8/1999 |
| EP | 0 980 894 B1 | 2/2000 |
| EP | 0988106 A1 | 3/2000 |
| EP | 1014941 A1 | 7/2000 |
| EP | 1070504 | 1/2001 |
| EP | 1127871 | 8/2001 |
| EP | 1138321 A | 10/2001 |
| EP | 1138321 A2 | 10/2001 |
| EP | 1152026 A1 | 11/2001 |
| EP | 1138321 A3 | 1/2002 |
| EP | 1166776 A2 | 1/2002 |
| EP | 1201233 A1 | 5/2002 |
| EP | 0661045 B1 | 7/2002 |
| EP | 1250045 | 10/2002 |
| EP | 1250045 A2 | 10/2002 |
| EP | 1251120 | 10/2002 |
| EP | 1293127 | 3/2003 |
| EP | 1293195 A1 | 3/2003 |
| EP | 1293196 A2 | 3/2003 |
| EP | 1127871 B1 | 9/2003 |
| EP | 1201233 B1 | 12/2004 |
| EP | 1251120 B1 | 12/2004 |
| EP | 1492506 B1 | 1/2005 |
| EP | 1166776 B1 | 2/2005 |
| EP | 1502592 A1 | 2/2005 |
| EP | 1658055 | 2/2005 |
| EP | 1515702 | 3/2005 |
| EP | 1527775 A1 | 4/2005 |
| EP | 1558221 A1 | 8/2005 |
| EP | 1558257 | 8/2005 |
| EP | 1560585 | 8/2005 |
| EP | 1658054 | 5/2006 |
| EP | 1138321 B1 | 1/2007 |
| EP | 1740161 | 1/2007 |
| EP | 1658055 B1 | 3/2007 |
| EP | 1765303 | 3/2007 |
| EP | 1786403 | 5/2007 |
| EP | 1558221 B1 | 6/2007 |
| EP | 1658054 B1 | 6/2007 |
| EP | 1842533 A2 | 10/2007 |

(56) References Cited

FOREIGN PATENT DOCUMENTS

| | | |
|---|---|---|
| EP | 1845955 | 10/2007 |
| EP | 1845956 | 10/2007 |
| EP | 1859789 | 11/2007 |
| EP | 1980245 A1 | 10/2008 |
| EP | 1897545 | 12/2008 |
| EP | 2131830 | 12/2009 |
| EP | 2249811 | 11/2010 |
| EP | 2273983 | 1/2011 |
| EP | 2402004 A2 | 1/2012 |
| ES | 2336571 | 12/2004 |
| ES | 2260042 | 11/2006 |
| ES | 2285497 | 11/2007 |
| ES | 2288621 | 1/2008 |
| ES | 2289542 | 2/2008 |
| ES | 2315505 | 4/2009 |
| GB | 1147210 A | 4/1969 |
| GB | 1567727 A | 5/1980 |
| GB | 2057878 | 4/1981 |
| HR | P20070272 | 6/2007 |
| HR | 20070456 | 11/2007 |
| JP | 03-501737 A | 4/1991 |
| JP | 8-505076 A | 6/1996 |
| JP | H09508410 A | 8/1997 |
| JP | 2002-275175 | 9/2002 |
| JP | 2003125706 A | 5/2003 |
| JP | 2005-314407 A | 11/2005 |
| JP | 2005534664 | 11/2005 |
| JP | 2007501201 A | 1/2007 |
| KR | 1020060069832 A | 6/2006 |
| KR | 20070039041 | 4/2007 |
| KR | 20070111510 | 11/2007 |
| KR | 20090085312 A | 8/2009 |
| KR | 20100111303 | 10/2010 |
| KR | 20110016921 | 2/2011 |
| MX | 2007000008 | 3/2007 |
| MX | 2007000009 | 3/2007 |
| MX | 2007009393 | 8/2007 |
| MX | 2010008138 | 8/2010 |
| MX | 2010012039 | 11/2010 |
| NO | 20061054 | 3/2006 |
| NO | 20070578 A | 1/2007 |
| NO | 20074412 A | 11/2007 |
| PT | 1699440 | 12/2004 |
| PT | 1658054 | 5/2006 |
| PT | 1658055 | 7/2007 |
| PT | 1515702 | 12/2008 |
| RU | 2131244 | 6/1999 |
| RU | 2396944 C2 | 7/2004 |
| RU | 2354357 | 12/2007 |
| RU | 2007103712 | 9/2008 |
| RU | 2007103707 | 11/2008 |
| RU | 2007132975 | 4/2009 |
| SI | 1515702 | 4/2009 |
| SI | 1699440 | 11/2009 |
| WO | 8000841 | 5/1980 |
| WO | 89/05624 | 6/1989 |
| WO | 90/03776 | 4/1990 |
| WO | 90/03776 A1 | 4/1990 |
| WO | 93/06723 | 4/1993 |
| WO | 93/10758 | 6/1993 |
| WO | 93/11749 | 6/1993 |
| WO | 93 23017 | 11/1993 |
| WO | 94/06414 | 3/1994 |
| WO | 94/08567 | 4/1994 |
| WO | 95/17174 A1 | 6/1995 |
| WO | 95/22319 | 8/1995 |
| WO | WO 95/20947 A1 | 8/1995 |
| WO | 95/30422 | 11/1995 |
| WO | 96/00066 | 1/1996 |
| WO | 96/03979 A1 | 2/1996 |
| WO | 96/14058 | 5/1996 |
| WO | WO 97/00673 | 1/1997 |
| WO | 97/33566 | 9/1997 |
| WO | 9749384 | 12/1997 |
| WO | 9835655 A3 | 2/1998 |
| WO | WO 98/20073 A2 | 5/1998 |
| WO | 98/28698 | 7/1998 |
| WO | 98/35655 A2 | 8/1998 |
| WO | 99/12864 A1 | 3/1999 |
| WO | 99/32120 | 7/1999 |
| WO | 99/44591 | 9/1999 |
| WO | 99/48481 | 9/1999 |
| WO | 00/33835 | 6/2000 |
| WO | 00/40205 | 7/2000 |
| WO | 01/08661 | 2/2001 |
| WO | 01/12230 | 2/2001 |
| WO | 01/15667 | 3/2001 |
| WO | 01/52651 | 7/2001 |
| WO | 01/97783 | 12/2001 |
| WO | 02/26061 | 4/2002 |
| WO | 02/26262 | 4/2002 |
| WO | 02/26928 | 4/2002 |
| WO | 0235991 A2 | 5/2002 |
| WO | 02/071860 A1 | 9/2002 |
| WO | 02/088217 A1 | 11/2002 |
| WO | WO 02/094254 A2 | 11/2002 |
| WO | 03/006723 | 1/2003 |
| WO | 03/013476 | 2/2003 |
| WO | 03/013479 | 2/2003 |
| WO | WO 03/015531 A2 | 2/2003 |
| WO | 03/024430 | 3/2003 |
| WO | 03024426 A1 | 3/2003 |
| WO | WO 03/018015 A1 | 3/2003 |
| WO | 03/026624 A1 | 4/2003 |
| WO | 03/028698 | 4/2003 |
| WO | 03/028990 A1 | 4/2003 |
| WO | 03/031546 | 4/2003 |
| WO | 03026743 A2 | 4/2003 |
| WO | 03/035029 | 5/2003 |
| WO | 03/035053 | 5/2003 |
| WO | 03/035054 | 5/2003 |
| WO | 03/035177 A2 | 5/2003 |
| WO | WO 03/039561 A1 | 5/2003 |
| WO | WO 03/049689 A2 | 6/2003 |
| WO | 03/053417 | 7/2003 |
| WO | 03/068392 | 8/2003 |
| WO | WO 03/070191 A1 | 8/2003 |
| WO | 03/092648 A1 | 11/2003 |
| WO | 03/094812 | 11/2003 |
| WO | 03/105808 | 12/2003 |
| WO | 2004/004693 A1 | 1/2004 |
| WO | 2004/043967 | 2/2004 |
| WO | 2004/026262 | 4/2004 |
| WO | 2004/026263 | 4/2004 |
| WO | 2004/037230 | 5/2004 |
| WO | 2004/037259 | 5/2004 |
| WO | 2004/037260 | 5/2004 |
| WO | 2004/066910 A2 | 8/2004 |
| WO | WO 2004/078212 A1 | 9/2004 |
| WO | 2004/084869 A1 | 10/2004 |
| WO | 2004/093801 A2 | 11/2004 |
| WO | 2004/093819 | 11/2004 |
| WO | 2004 098567 A2 | 11/2004 |
| WO | 2004/100894 A2 | 11/2004 |
| WO | 2005/016313 | 2/2005 |
| WO | 2005/016314 | 2/2005 |
| WO | 2005/032524 A2 | 4/2005 |
| WO | 2005/065646 A2 | 4/2005 |
| WO | 2005/041968 | 5/2005 |
| WO | 2005/053587 A1 | 6/2005 |
| WO | 2005/053656 A1 | 6/2005 |
| WO | 2005/055981 A2 | 6/2005 |
| WO | 2005/063214 | 7/2005 |
| WO | 2005/066183 | 7/2005 |
| WO | WO 2005/060942 A1 | 7/2005 |
| WO | 2005 079760 A1 | 9/2005 |
| WO | 2005/102286 | 11/2005 |
| WO | 2005102294 | 11/2005 |
| WO | 2005105036 A1 | 11/2005 |
| WO | WO 2005/102294 A2 | 11/2005 |
| WO | 2006/002883 | 1/2006 |
| WO | 2006/002884 | 1/2006 |
| WO | 2006/002886 | 1/2006 |
| WO | 2006002884 | 1/2006 |

(56) References Cited

FOREIGN PATENT DOCUMENTS

| | | |
|---|---|---|
| WO | WO 2006/002884 B1 | 3/2006 |
| WO | WO 2006/039692 A2 | 4/2006 |
| WO | 2006058249 A2 | 6/2006 |
| WO | 2006/082097 | 8/2006 |
| WO | 2006/082099 | 8/2006 |
| WO | WO 2006/105615 A1 | 10/2006 |
| WO | 2007/005716 A2 | 1/2007 |
| WO | 2007/008752 | 1/2007 |
| WO | WO 2007/014061 A2 | 2/2007 |
| WO | 2007/045462 A2 | 4/2007 |
| WO | 2007/048233 | 5/2007 |
| WO | 2007/053698 | 5/2007 |
| WO | 2007/045462 A3 | 6/2007 |
| WO | 2007/085024 A2 | 7/2007 |
| WO | 2007085024 A3 | 7/2007 |
| WO | 2007103105 A2 | 9/2007 |
| WO | 2007103286 | 9/2007 |
| WO | 2007/112285 | 10/2007 |
| WO | 2008 023261 A1 | 2/2008 |
| WO | 2008033523 A1 | 3/2008 |
| WO | WO 2008/069941 A2 | 6/2008 |
| WO | 2008/086804 A2 | 7/2008 |
| WO | 2008/107149 A2 | 9/2008 |
| WO | 2008107149 | 9/2008 |
| WO | 2008107149 A3 | 9/2008 |
| WO | WO 2008/142627 A2 | 11/2008 |
| WO | 2008/148798 A2 | 12/2008 |
| WO | WO 2009/005803 A1 | 1/2009 |
| WO | WO 2009/014534 A1 | 1/2009 |
| WO | WO 2009/051819 A1 | 4/2009 |
| WO | 2009/092601 A1 | 7/2009 |
| WO | 2009092601 | 7/2009 |
| WO | 2009112273 A2 | 9/2009 |
| WO | WO 2009/110005 A2 | 9/2009 |
| WO | 2009/135680 A1 | 11/2009 |
| WO | 2009135680 | 11/2009 |
| WO | 2010057036 A2 | 5/2010 |
| WO | 2010140007 A2 | 12/2010 |
| WO | 2010140007 A9 | 12/2010 |
| WO | 2011009602 | 1/2011 |
| WO | 2011009603 | 1/2011 |
| WO | 2011009604 | 1/2011 |
| WO | 2011095314 A3 | 8/2011 |
| WO | 2011/109441 A1 | 9/2011 |
| WO | 2012028317 A1 | 3/2012 |
| WO | 2012028318 A1 | 3/2012 |
| WO | WO 2013/017234 A1 | 2/2013 |

OTHER PUBLICATIONS

Maggi. Therapeutic Potential of Capsaicin-like Molecules. 1Life Sciences, vol. 51, pp. 1777-1781, 1992.
Katz et al., Clin. J. Pain, 23(8): 648-660 (2007).
Arnold, "Teen Abuse of Painkiller OxyContin on the Rise," www.npr.org, Dec. 19, 2005.
Baum et al., Public Health Reports, 102(4): 426-429 (1987).
Purdue News, "Purdue Pharma Provides Update on Development of New Abuse-Resistant Pain Medications; FDA Cites Patient Needs as First Priority; New Drug Application Delayed," www.headaches.about.com, Jun. 18, 2002.
Strang, British Med. J., 302: 969 (1991).
Tompkins et al., Psychopharma., 210: 471-480 (2010).
Waters et al., Am. J. Psychiatry, 164(1): pp. 173-174 (2007).
El-Egakey, Adel et al, Pharmacerutica Acta Helvetiae, vol. 46, Mar. 19, 1070.
Apicella A., Biomaterials, vol. 14, No. 2, pp. 83-90, 1993.
Bailey F.E., Journal of Applied Polymer Science, vol. 1, Issue No. 1, pp. 56-62, 1959.
Bauer, Coated Pharmaceutical Dosage Forms, CRC Press, 1998, 1-10.
Braun, et al. Angel Orthodontist, vol. 65 (5) pp. 373-377, 1995.
Crowley M.M., Biomaterials 23, 2002, pp. 4241-4248.
Coppens, Pharmaceutical Technology, 62-70, Jan. 2005.
Caraballo, Journal of Controlled Release, vol. 69, pp. 345-355, 2000.
DOW Technical Data, POLYOX, Feb. 2003.
Dow Excipients Chem. of Poly. Water Soluble-Resin 2004.
Dejong (Pharmaceutisch Weekblad Scientific Edition 1987, p. 24-28.
Davies, et al; European Journal of Pharmaceutics and Biopharmaceutics, 67, 2007, pp. 268-276.
Efentakis M.,Pharmaceutical Development and Technology, 5 (3), pp. 339-346, 2000.
European Pharmacopoeia, pharmaceutical technical procedures, 1997, 135.
El-Sherbiny, European Polymer Journal, vol. 41, pp. 2584-2591, 2005.
Follonier N., Drug Development and Industrial Pharmacy, 20(8), pp. 1323-1339, 1994.
Follonier N., Journal of Controlled Release 36, pp. 243-250, 1995.
Fell, et al, Journal of Pharmaceutical Sciences, vol. 59, No. 5, May 1970, pp. 688-691.
Graham N.B., Poly(Ethylene Glycol) Chemistry: Biotechnical and Biomedical Applications, Chapter 17, 1992.
Griffith, Drug Administration, vol. 19, No. 1, pp. 41-42, 2003.
Hanning C.D., British Journal of Anaesthesia, 61, pp. 221-227, 1988.
Janicki S., Acta Pharm. Technol. 33 (3) 154-155, 1987.
Kim C.-J. J Pharm. Sciences 1995, 84(3).
Kim, Chem. Pharm Bull. 1992, 40(10), 2800-2804.
J.W. McGinity—Letter of Jan. 26, 2009.
Levina, Journal of Pharmaceutical Sciences, vol. 89, No. 6, pp. 703-723, Jun. 2000.
Levina, Drug Development and Industrial Pharmacy, vol. 28, No. 5, pp. 495-514, 2002.
Madorsky S.L., Journal of Polymer Science, vol. 84, No. 3, Mar. 1959.
Mank R., Pharmazie 44, H. 11, pp. 773-776, 1989.
Mank R., Pharmazie 45, H. 8, pp. 592-593 1990.
Mesiha M.S., Drug Development and Industrial Pharmacy, 19(8), pp. 943-959, 1993.
Moroni A., Drug Development and Industrial Pharmacy, 21(12) pp. 1411-1428, 1995.
Maggi et al., Biomaterials, 2002, 23, 1113-1119.
Miller, Nursing, pp. 50-52, Feb. 2000.
Mitchell, Special Resource, vol. 35, No. 5, pp. 535-557, 2000.
Verna, Manthena et al, Am. J. Drug Deliv. 2004: 2 (1): 43-57.
Ohnishi N., Chem. Pharm. Bull, 35(8), pp. 3511-3515, 1987.
Ozeki T., Journal of Controlled Release 58, pp. 87-95, 1999.
Prapaitrakul W., J. Pharm. Pharmacol. 43, pp. 377-381, 1991.
Proeschel, J. Dent. Res., vol. 81, No. 7, pp. 464-468, 2002.
Remington's Pharmaceutical Sciences, pp. 1553-1593, Ch. 89, 1980, 16th Edition.
Radko S., Applied ad Theoretical Electrophoresis 5, pp. 79-88, 1995.
Remington's Pharmaceutical Sciences 17th ed., 1418 (1985).
Rippie E.G., Journal of Pharmaceutical Sciences, Vo. 58, No. 4, pp. 428-431, Apr. 1969.
Schreirs J., Polymer, vol. 32, No. 11, 1991.
Shivanand P.Pharmaceutical Research, Oct. 1991, vol. 8, No. 10.
Sprockel O.L., J. Pharma. Pharmacol. 42, pp. 152-157, 1990.
Stringer J.L., Journal of Controlled Release 42, pp. 195-202, 1996.
Summers et al; Journal of Pharmaceutical Sciences, vol. 66, No. 8, Aug. 1977, pp. 1172-1175.
Third Party Observations, Feb. 2, 2009.
Thoma V.K., Pharm. Ind. 51, Nr. 3, 1989.
US Pharmacopoeia, Chapter 1217, Aug. 1, 2008.
Wikipedia—inert gas data sheet , Dec. 2009.
Yang, Journal of Pharmaceutical Sciences, vol. 85, No. 10, Oct. 1996.
Yarbrough et al, Letters to Nature 322, 347-349 (Jul. 24, 1986) "Extraordinary effects of mortar-and -pestle grinding on microstructure of sintered alumina gel".
Zhang et al., Pharmaceutical Development and Technology, 1999, 4, 241-250.
Tablet, www.docstoc.com (2011).
Dachille, F. et al., "High-Pressure Phase Transformation in Laboratory Mechanical Mixers and Mortars", 1906., Nature, 186, pp. 1-2 (abstract).
Ohnishi N. Chem Pharm. Bull, 35(8), pp. 3511-3515, 1987.

(56) References Cited

OTHER PUBLICATIONS

Conversion of 18.8 kiloponds to newtons, http://www.unitconversion.org/force/newtons-to-kiloponds-conversion.html on Jul. 5, 2011.
Waltimo et al. A novel bite force recorder and maximal isometric bite force values for healthy young adults. Scand J Dent Res. 1993, vol. 101, pp. 171-175.
Waltimo et al. Maximal bite force and its association with signs and symptoms of crandiomandibular disorders in young Finnish non-patients. Acta Odonol. Scand. 1995, vol. 53, pp. 254-258.
Wu et al. Mathematical modeling and in vitro study of controlled drug release via a highly swellable and dissoluble polymer matrix: polyethylene oxide with high molecular weights. Journal of Controlled Release. 2005. vol. 102, pp. 569-581.
Ravin, Louis. Preformulation. Chapter 76. In Remington's Pharmaceutical Sciences, 17th Ed, 1985.
Disanto, Anthony. Bioavailability and Bioequivalency Testing. Chapter 77. In Remington's Pharmaceutical Sciences, 17th Ed, 1985.
Knevel, Adelbert. Separation. Chapter 78. In Remington's Pharmaceutical Sciences, 17th Ed, 1985.
Phillips, G. Briggs. Sterilization. Chapter 79. In Remington's Pharmaceutical Sciences, 17th Ed, 1985.
Siegel, Frederick. Tonicity, Osmoticity, Osmolality, and Osmolarity. Chapter 80. In Remington's Pharmaceutical Sciences, 17th Ed, 1985.
Giles et al. Plastic Packaging Materials. Chapter 81. In Remington's Pharmaceutical Sciences, 17th Ed, 1985.
Lintner, Carl. Stability of Pharmaceutical Products. Chapter 82. In Remington's Pharmaceutical Sciences, 17th Ed, 1985.
Erskine, Jr., Clyde. Quality Assurance and Control. Chapter 83. In Remington's Pharmaceutical Sciences, 17th Ed, 1985.
Nairn, J.G., Solutions, Emulsion, Suspensions and Extractives. Chapter 84. In Remington's Pharmaceutical Sciences, 17th Ed, 1985.
Avis, Kenneth. Parenteral Preparations. Chapter 85. In Remington's Pharmaceutical Sciences, 17th Ed, 1985.
Turco et al. Intravenous Admixtures. Chapter 86. In Remington's Pharmaceutical Sciences, 17th Ed, 1985.
Mullins, John. Ophthalmic Preparations. Chapter 87. In Remington's Pharmaceutical Sciences, 17th Ed, 1985.
Block, Lawrence. Medicated Applications. Chapter 88. In Remington's Pharmaceutical Sciences, 17th Ed, 1985.
Rippie, Edward. Powders. Chapter 89. In Remington's Pharmaceutical Sciences, 17th Ed, 1985.
King et al. Oral Solid Dosage Forms. Chapter 90. In Remington's Pharmaceutical Sciences, 17th Ed, 1985.
Porter, Stuart. Coating of Pharmaceutical Dosage Forms. Chapter 91. In Remington's Pharmaceutical Sciences, 17th Ed, 1985.
Longer et al. Sustained-Release Drug Delivery Systems. Chapter 92. In Remington's Pharmaceutical Sciences, 17th Ed, 1985.
Sciarra et al. Aerosols. Chapter 93. In Remington's Pharmaceutical Sciences, 17th Ed, 1985.
João F. Pinto et al.,"Evaluation of the Potential Use of Poly(ethylene oxide) as Tablet- and Extrudate-Forming Material," AAPS PharmSci, 2004; 6 (2), Article 15, pp. 1-10, (http://www.aapspharmsci.org).
European Search Report of related EP Application No. 12 00 2708 dated Sep. 24, 2012.
Yang et al., "Zero-Order Release Kinetics from a Self-Correcting Floatable Asymmetric Configuration Drug Delivery System", Journal of Pharmaceutical Sciences, vol. 85, No. 2, Feb. 1996, pp. 170-173.
Bennet et al., "A peripheral mononeuropathy in rat that produces disorders of pain sensation like those seen in man", Pain, 33 (1988), pp. 87-107.
Carey et al., Advanced Organic Chemistry, Part A: Structure and Mechanism, Fifth Edition, 2007, Table of Contents, pp. i-xxi.
Carey et al., Advanced Organic Chemistry, Part B: Reactions and Synthese, Fifth Edition, 2007, Table of Contents, pp. i-xxx.
Cheng et al., "Relationship Between the Inhibition Constant (KI) and the Concentration of Inhibitor which Causes 50 Per Cent Inhibition (I50) of an Enzymatic Reaction", Biochemical Pharmacology, vol. 22, 1973, pp. 3099-3108.

Dachille et al., "High-pressure Phase Transofromations in Laboratory Mechanical Mixers and Mortars", Nature, vol. 186, Apr. 2, 1960, pp. 34 and 71.
D'Amour et al., "A Method for Determining Loss of Pain Sensation", Loss of Pain Sensation, 1941, pp. 74-79.
Dubuisson et al., "The Formalin Test: A Quantitative Study of the Analgesic Effects of Morphine, Meperidine, and Brain Stem Stimulation in Rats and Cats", Pain, 4 (1977), pp. 161-174.
Kim et al., "An Experimental Model for Peripheral Neuropathy Produced by Segmental Spinal Nerve Ligation in the Rat", Pain, 50 (1992), pp. 355-363.
Liu et al., "Properties of Lipophilic Matrix Tables Containing Phenylpropanolamine Hydrochloride Prepared by Hot-Melt Extrusion", European Journal of Pharmaceutics and Biopharmaceutics, 52 (2001), pp. 181-190.
Repka et al., Bioadhesive Properties of Hydroxypropylcellulose Topical Films Produced by Hot-Melt Extrusion, Journal of Controlled Release, 70 (2001), pp. 341-351.
Smith et al., March's Advanced Organic Chemistry, Sixth Edition, 2007, Table of Contents, pp. xiii-xiv.
Smith, Compendium of Organic Synthetic Methods, vol. 12, Wiley, 2009, Table of Contents, pp. i-xviii.
PCT International Search Report and Written Opinion for PCT Application No. PCT/EP2013/057851 dated Jun. 12, 2013.
Kalant et al., Death in Amphetamine Users: Causes and Rates, CMA Journal, vol. 112, Feb. 8, 1975 pp. 299-304.
Deighan, C.J. et al., Rhabdomyolysis and acute renal failure resulting from alcohol and drug abuse, Q.J. Med, vol. 93, 2000, pp. 29-33.
Woodburn, K.R., Vascular complications of injecting drug misuse, Br. J. of Surgery, vol. 83, 1996, pp. 1329-1334.
Dow Chemical Company, Dow Excipients for Controlled Release of Drugs in Hydrophilic Matrix Systems, 2006, pp. 1-36.
Sax et al., Hawley's Condensed Chemical Dictionary, 11th ed., 1987, p. 1233, definition of "wax".
Riippi et al., The effect of compression force on surface structure, crushing strength, friability and disintegration time of erythromycin acistrate tablets, Eur J Pharm Biopharm, vol. 46, 1998, pp. 339-345.
Goodman and Gilman, "The Pharmacological Basis of Therapeutics, Seventh Edition", MacMillan Publishing Company, Chapter 22, pp. 491-530. 1985.
Goodman and Gilman, "The Pharmacological Basis of Therapeutics, Seventh Edition", MacMillan Publishing Company, Chapter 23, pp. 533-579. 1985.
Rowe et al., Handbook of Pharmaceutical Excipients, Seventh Edition, 2012, Table of Contents.
Costa et al., Eur. J. Pharm. Sci, 2001, 13(2), 123-133.
Encyclopedia of Pharmaceutical Technology, Informa Healthcare, 1$^{st}$ Edition, 1996, Table of Contents.
Note for Guidance on Stability Testing, EMEA, Aug. 2003, pp. 1-20.
Bauer et al. Lehrbuch der Pharmazeutischen Technologie. Eight Edition 2006. Stuttgart, pp. 343-352.
Hartauer, Pharma. Dev. & Tech, 5 (3) 303-310 (2000).
Marques, Tablet breaking force, 2008.
Ritschel et al. Die Tablette: Handbuch der Entwicklung, Herstellung und Qualitatssicherung, 2nd Edition, 2002, Ch 6, pp. 69-82 and 115-136.
Ritschel et al. Die Tablette: Handbuch der Entwicklung, Herstellung und Qualitatssicherung, 2nd Edition, 2002, Table of content.
Wagner, Pharmazeutische Biologie—Drogen und ihre Inhaltsstoffe—Scharfstoffdrogen, 2nd., revised edition, Gustav Fischer Verlag, Stuttgart-N.Y., 1982,Table of Content.
Zeeshan, F and N. Bukhari. "Development and Evaluation of a Novel Modified-Release Pellet-Based Tablet System for the Delivery of Loratadine and Pseudophedrine Hydrochloride as Model Drugs," AAPS PharmSciTech 11(2); 910-916 (available on-line May 22, 2010).
Polyox water-soluble resins (DOW Mar. 2002); see http://msds-search.dow.com/PublishedLiteratureDOWCOM/dh_0031/0901b8038003 1a4a.pdf?filepath=/326-00001.pdf &fromPage=GetDoc).
Swarbrick, Encyclopedia of Pharmaceutical Technology, Informa Healthcare, 1988, 1st edition, vol. 1, table of contents.

(56) References Cited

OTHER PUBLICATIONS

Swarbrick, Encyclopedia of Pharmaceutical Technology, Informa Healthcare, 1988, 1st edition, vol. 2, table of contents.
Swarbrick, Encyclopedia of Pharmaceutical Technology, Informa Healthcare, 1988, 1st edition, vol. 3, table of contents.
Swarbrick, Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.
Swarbrick, Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents.
Swarbrick, Encyclopedia of Pharmaceutical Technology, Informa Healthcare, 1988, 1st edition, vol. 9, table of contents.
Swarbrick, Encyclopedia of Pharmaceutical Technology, Informa Healthcare, 1988, 1st edition, vol. 10, table of contents.
Swarbrick, Encyclopedia of Pharmaceutical Technology, Informa Healthcare, 1988, 1st edition, vol. 11, table of contents.
Swarbrick, Encyclopedia of Pharmaceutical Technology, Informa Healthcare, 1988, 1st edition, vol. 12, table of contents.
Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st edition, vol. 14, table of contents.
Swarbrick, Encyclopedia of Pharmaceutical Technology, Informa Healthcare, 1988, 1st edition, vol. 15, table of contents.
Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Swarbrick, Encyclopedia of Pharmaceutical Technology, Informa Healthcare, 1988, 1st edition, vol. 19, table of contents.
Swarbrick, Encyclopedia of Pharmaceutical Technology, Informa Healthcare, 1988, 1st edition, vol. 20, table of contents.
Almeida, A. et al., Ethylene vinyl acetate as matrix for oral sustained release dosage forms produced via hot-melt extrusion, European Journal of Pharmaceutics and Biopharmaceutics 77 (2011) 297-305.
Almeida, A. et al., Sustained release from hot-melt extruded matrices based on ethylene vinyl acetate and polyethylene oxide, European Journal of Pharmaceutics and Biopharmaceutics 82 (2012) 526-533.
Sreevivasa, B. et al, Design and evaluation of ethylene vinyl acetate sintered matrix tablets, Indian Journal of Pharmaceutical Sciences, Sep.-Oct. 2003, 65(5): 496-502.
European Search Report and Written Opinion for EP Application No. 13169659.3, Aug. 6, 2013.
European Search Report and Written Opinion for EP Application No. 13169658.3, Aug. 6, 2013.
Spassov et al., Stereochemistry of Diastereomeric 3-Dialkylaminopropanols and O-Derivatives, J.f. prakt. Chemie, 323:5, 793-800 (1981).
Foye, W., Principles of Medicinal Chemistry; Structural Features and Pharmacologic Activity, p, 63-66 at 65 (1989).
Foye, W., Principles of Medicinal Chemistry; Analgesics p. 241-242, at 241 (1989).
Remington, The Science and Practice of Pharmacy, 19th ed., vol. II, p. 1457 (1995) (providing a table of DFA-approved commercially marketed salts).
Evonik Industries, Eudragit Application Guidelines, 10th Edition, 2008, Table of Contents.
Tikhonov, A. et al., Biopharmacy. The Manual for Students of Pharmaceutical Universities and Departments. 2003, pp. 40-41, Kharkov, Ukraine. (Full English translation attached.).
Tranquilan-Aranilla et al., "Kappa-carrageenan-polyethylene oxide hydrogel blends prepared by gamma irradiation," Radiation Physics and Chemistry vol. 55, pp. 127-131, 1999.
Application of a modeling system in the formulation of extended release hydrophilic matrices, Reprinted from Pharmaceutical Technology Europe, Jul. 2006.
Application of Opadry II, complete film coating system, on metformin HCI extended release matrices containing Polyox water soluble resin, Colorcon Apr. 2009.
Evaluation of Verapamil HCI (240 mg) Extended Release Matrix Formulation Using USP Apparatus III in Biorelevant Dissolution Media, Jul. 2009.
Formulation of Polyox ER Matrices for a Highly Soluble Active, Colorcon Jul. 2009.
Investigation of a Directly Compressible Metformin HCI 500mg Extended Release Formulation Based on Hypromellose, Colorcon Jul. 2009.
Metformin Hydrochloride 750 mg Extended Release Tablets, Lubrizol Advanced Materials, Inc., Sep. 2010.
Metformin Hydrochloride 1000 mg Extended Release Tablets, Lubrizol Advanced Materials, Inc., Nov. 20, 2009, Previous Edition Dec. 19, 2008.
Pentoxifylline 400 mg Extended Release Tablets, Lubrizol Advanced Materials, Inc., Mar. 3, 2011, Previous Edition Nov. 19, 2009.
Perez-Marcos, B., Usefulness of certain varieties of Carbomer in the formulation of hydrophilic furosemide matrices, International Journal of Pharmaceutics, 67 (1991) 113-121.
Physico-mechanical Characterization of Polyox for Table Manufacture, Colorcon Jul. 2009.
Tramadol Hydrochloride 100 mg Extended Release Tablets, Lubrizol Advanced Materials, Inc., Sep. 2010.
European Search Report, Application No./Patent No. 12003743.7-1219, Sep. 24, 2012.
Henrist et al. In vitro and in vivo evaluation of starch-based hot stage extruded double matrix systems. Journal of Controlled Release. 2001, vol. 75, pp. 391-400.
McNeill et al. Properties controlling the diffusion and release of water-soluble solutes from poly(ethylene oxide) hydrogels. 4. Extended constant rate release from partly-coated spheres. Journal Biomat. Sci. Polym. Ed. 1996, vol. 7, pp. 953-963.
Pillay et al. A novel approach for constant rate delivery of highly soluble bioactives from a simple monolithic system. Journal of Controlled Release. 2000, vol. 67, pp. 67-78.
O.G. Piringer, A.L. Baner, Plastic Packaging: Interactions with Food and Pharmaceuticals, Wiley VCH, 2nd Completely Revised Edition, Feb. 13, 2008.
Guidance for Industry—Bioavailability and Bioequivalence—Studies for Orally Administered Drug Products—General Considerations, FDA, BP, Announced in the Federal Register: vol. 68, No. 53/Mar. 19, 2003.
Crowley MM,Drug Dev Ind Pharm. Sep. 2007;33(9):909-26.
D.A. Dean, E.R. Evans, I.H. Hall, Pharmaceutical Packaging Technology, Taylor & Francis, 1st Edition, Nov. 30, 2000.
Dexheimer, Terahertz Spectroscopy: Principles and Applications (Optical Science and Engineering Series), CRC; 1 edition 2007.
Encyclopedia of Pharmaceutical Technology, Third Edition, vol. 1, edited by James Swarbrick. Informa Healthcare, 3rd Edition, Oct. 25, 2006.
Encyclopedia of Pharmaceutical Technology, Third Edition, vol. 2, edited by James Swarbrick. Informa Healthcare, 3rd Edition, Oct. 25, 2006.
Encyclopedia of Pharmaceutical Technology, Third Edition, vol. 3, edited by James Swarbrick. Informa Healthcare, 3rd Edition, Oct. 25, 2006.
Encyclopedia of Pharmaceutical Technology, Third Edition, vol. 4, edited by James Swarbrick. Informa Healthcare, 3rd Edition, Oct. 25, 2006.
Encyclopedia of Pharmaceutical Technology, Third Edition, vol. 5, edited by James Swarbrick. Informa Healthcare, 3rd Edition, Oct. 25, 2006.
Encyclopedia of Pharmaceutical Technology, Third Edition, vol. 6, edited by James Swarbrick. Informa Healthcare, 3rd Edition, Oct. 25, 2006.
Y.-S. Lee et al., Principles of Terahertz Science and Technology (Lecture Notes in Physics), Springer; 1 edition 2008.

(56) References Cited

OTHER PUBLICATIONS

R.E. Miles et al., Terahertz Frequency Detection and Identification of Materials and Objects (NATO Science for Peace and Security Series B: Physics and Biophysics), Springer; 1 edition 2007.
Guidance for Industry—Statistical Approaches to Establishing Bioequivalence, FDA, BP, Jan. 2001.
Note for Guidance on the Investigation of Bioavailability and Bioequivalence, EMEA, London, Jul. 26, 2001 (CPMP/EWP/QWP/1401/98.
Andre et al., "O-Demethylation of Opiod Derivatives With Methane Suffonic Acid/Methoinine: Application to the Synthesis of Naloxone and Analogues" Synthetic Comm. 22(16), pp. 2313-2327, 1992.
Augustine, R.L., Catalytic Hydrogenation of a, B-Unsaturated Ketones. III The Effect of Quantity and Type of Catalysts, J.Org Chem. 28(1), pp. 152-155, Abstract 1963.
Goodman and Gilman, "The Pharmacological Basis of Therapeutics, Seventh Edition", MacMillan Publishing Company, Table of Contents. 1985.
McGinity et al., Hot-Melt Extrusion as a Pharmaceutical Process, American Phamnaceutical Review, vol. 4 (2), pp. 25-36, 2001.
Weiss, U., "Derivatives of Morphine. I 14-Dihydroxydihydromorphinone," J. Am. Chem. Soc. 77, pp. 5891-5892, Nov. 20, 1955.
European Search Report, Application No./Patent No. 11006253.6-2112, Dec. 16, 2011.
European Search Report, Application No./Patent No. 11006254.4-2112, Dec. 16, 2011.
European Search Report, Application No./Patent No. 11008131.2-1219, Feb. 24, 2012.
European Search Report, Application No./Patent No. 12001296.8-1219, Jun. 26, 2012.
European Search Report, Application No./Patent No. 11009129.5-2112, Apr. 10, 2012.
European Search Report, Application No./Patent No. 12001301.6-1219, Jun. 26, 2012.
A. James, "The legal and clinical implications of crushing tablet medication", Nurse Times 100(50), 28-33, 2004.
C. W. McGary, Jr. "Degradation of Poly(ethylene Oxide)", Journal of Polymer Science vol. XLVI, 1960, pp. 51-57.
P. Cornish "Avoid the Crush": hazards of medication administration in patients with dysphagia or a feeding tube, CMA Media Inc., CMAJ. 172(7), pp. 871-872, 2005.
European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
Griffin, "Classification of Surface-Active Agents by HLB" Journal of the Society of Cosmetic Chemists, Atlas Powder Company, 1949, pp. 311-326.
Griffith et al. "Tablet Crushing and the Law: The Implications for Nursing" Professional Nurse 19(1), pp. 41-42, 2003.
Mitchell, "Oral Dosage Forms That Should Not Be Crushed: 2000 Update" Hospital Pharmacy 35(5), 553-557, 2000.
Munjal et al. "Polymeric Systems for Amorphous Delta9—Tetrahydrocannabinol Produced by a Hot-Melt Method. Part II: Effect of Oxidation Mechanisms and Chemical Interactions on Stability" Journal of Pharmaceutical Sciences vol. 95 No. 11, Wiley InterScience, 2006, pp. 2473-2485.
Ozeki et al. "Control of Medicine Release From Solid Dispersion Through Poly(ethyleneoxide)-Carboxyvinylpolymer Interaction", International Journal of Pharmaceutics, 165, 1998, pp. 239-244.
Ozeki et al. "Controlled Release From Solid Dispersion Composed of Poly(ethylene oxide)-Carbopol Interpolymer Complex With Various Cross-Linking Degrees of Carbopol", Journal of Controlled Release. 63, 2000. pp. 287-295.
Munsell Color Company, "The Munsell Book of Color: Glossy Collection", X-Rite, Originally published in 1966, pp. 1-7.
Schier et al. "Fatality from Administration of Labetalol and Crushed Extended-Release Nifedipine" The Annals of Pharmacotherapy vol. 37, 1420-1423, Oct. 2003.

"The Dissolution Procedure: Development and Validation", heading "Study Design", "Time Points" US Pharmacopoeia (USP), General Chapter 1092, pp. 1-15, 2006.
Wade and Weller, "Handbook of Pharmaceutical Excipients: 2nd Edition", The American Pharmaceutical Association and the Pharmaceutical Press, Table of Contents pp. v-vi, 1994.
Yeh et al., Stability of Morphine in Aqueous Solution III: Kinetics of Morphine Degradation in Aqueous Solution, Wiley Subscription Services, Inc., Journal of Pharmaceutical Sciences, 50(1): 35-42 (1961).
Tipler, et al, Physics for Scientists and Engineers, 6th Edition, pp. 234-235, 2003.
Stafford J., überzogene feste Formen, 1991, 347-68.
Schroeder J.,Granulierung hydrophober Wirkstoffe im Planetwalzenextruder 2003, vol. 65, No. 4, 367-372.
Rowe et al. Handbook of Pharmaceutical Excipients. Sixth Edition. 2009, pp. v-ix, Table of Contents.
Herbert A. Lieberman, Pharmaceutical Dosage Forms, Tablets, Second Edition, Revised and Expanded, 1990.
Brown, "The Dissolution Procedure: Development and Validation" vol. 31(5). Chapter 1092, 2006, pp. 1-15.
Ritschel et al. Die Tablette: Handbuch der Entwicklung, Herstellung und Qualitatssicherung. 2002, Ch 6, pp. 515-519.
Bauer et al. Lehrbuch der Pharmazeutischen Technologie. 1999. pp. IX-XV, Table of contents.
European Pharmacopoeia, Third Edition, Council of Europe, Strasbourg, 1997, pp. 127-152.
European Pharmacopoeia, Third Edition Supplement 2000, Council of Europe, Strasbourg, 2000, pp. 85-107.
Hong et al. Dissolution kinetics and physical characterization of three-layered tablet with poly(ethylene oxide) core matrix capped by Carbopol. Int .J. Pharmacol. 2008, vol. 356, pp. 121-129.
Hoepfner et al. Fiedler Encyclopedia of Excipients. 2007, Table of Contents only.
Cawello, "Parameters for Compartment-free Pharmacokinetics—Standardization of Study Design, Data Analysis and Reporting" 1999, pp. XI-XIII (table of contents).
Pharm. Research, Official Journal of the American Association of Pharmaceutical Scientists, Sep. 1989, 6(9), S-98.
Pharm. Research, Official Journal of the American Association of Pharmaceutical Scientists, Oct. 1991, 8(10), S-192.
Wagner, Pharmazeutische Biologie—Drogen und ihre Inhaltsstoffe—Scharfstoffdrogen, 1982, pp. 82-92.
Lockhart et al, "Packaging of Pharmaceuticals and Health Care Products"; Blackie Academic & Professional; First Edition 1996.
International Search Report and Written Opinion for Application No. PCT/EP2010/004459 dated Dec. 1, 2010.
International Search Report and Written Opinion for Application No. PCT/EP2013/053894 dated Mar. 22, 2013.
European Search Report and Written Opinion for EP Application No. 13176309.9-1460, Oct. 9, 2013.
PCT International Search Report and Written Opinion for PCT Application No. PCT/EP2013/059728 dated Aug. 6, 2013.
"Polyox water soluble resins" 2003. http://www.dow.com/webapps/lit/litorder.asp?filepath=polyox/pdfs/noreg/326-00002.pdf.
PCT International Search Report and Written Opinion for PCT Application No. PCT/EP2009/003290 dated Jul. 9, 2009.
Committee for Proprietary Medicinal Products. Note for Guidance on the Investigation of Bioavailability and Bioequivalence. 2001, pp. 1-18.
Albertini, B. "New spray congealing atomizer for the microencapsulation of highly concentrated solid and liquid substances," European Journal of Pharmaceutics and Biopharmaceutics 69 (2008) 348-357.
Jannetto, P. et al, "Oxycodone: Recognition and Pharmacogenomics," Toxicology News, Mar. 2003, 1-7.
Kolter, K., "Compression Behaviour of Kollidon SR," APV/ APGI 2002, Florence, Apr. 11, 2002.
Oxycontin: Balancing Risks and Benefits, United States Senate, Hearing, Feb. 12, 2002.
Pontier, C. et al, "Use of cycles of compression to characterize the behavior of apatitic phosphate powders," Journal of the European Ceramic Society 22 (2002), 1205-1216.

(56) References Cited

OTHER PUBLICATIONS

Silver, J. "Painkiller OxyContin 'most commonly abused prescription drug on the streets of Western Pennsylvania'", Pittsburg Post-Gazette, Apr. 8, 2001.

Wikipedia-Dextromethorphan Aug. 12, 2013 (and attached related English-language entry dated Dec. 11, 2013).
Handbook of Pharmaceutical Excipients, 1986, American Pharmaceutical Association, Washington, DC and London (Table of Content Only).

* cited by examiner

DOSAGE FORM WITH IMPEDED ABUSE

CROSS REFERENCE TO RELATED APPLICATION

This application claims priority from Federal Republic of Germany patent application no. DE 10 2007 011 485.2, filed Mar. 7, 2007, the entire disclosure of which is incorporated herein by reference.

BACKGROUND OF THE INVENTION

The present invention relates to a multiparticulate dosage form with impeded abuse containing, in addition to one or more active substances having abuse potential (A), optionally at least one physiologically acceptable auxiliary (B), at least one synthetic or natural polymer (C), optionally at least one wax (D) and at least one disintegrating agent (E), with the individual particles of the dosage form having a breaking strength of at least 500 N and a release of the active substance of at least 75% after 45 minutes, and relates to processes for the preparation of the dosage form according to the invention.

A large number of pharmaceutical active substances not only have an outstanding efficacy in their relevant field of application, but also a potential for being abused, i.e. an abuser can use them to produce effects which are not consistent with their intended use. Thus, for example opiates which exhibit an excellent efficacy in controlling severe to extremely severe pain, are frequently abused to induce euphoric states similar to being intoxicated. In particular, active substances which have a psychotropic effect are abused accordingly.

To enable abuse, the corresponding dosage forms, such as tablets or capsules are crushed, for example ground by the abuser, the active substance is extracted from the thus obtained powder using a preferably aqueous liquid and after being optionally filtered through cotton wool or cellulose wadding, the resultant solution is administered parenterally, in particular intravenously. This type of dosage results in an even faster diffusion of the active substance compared to the oral abuse, with the result desired by the abuser, namely the kick. This kick or these intoxication-like, euphoric states are also reached if the powdered dosage form is dosage nasally, i.e. is sniffed.

To prevent these possibilities of abuse, it is proposed in U.S. Pat. No. 4,070,494 to add an agent capable of swelling to the dosage form. This agent swells when water is added to extract the active substance which means that the filtrate separated from the gel contains only a very small amount of active substance.

A corresponding approach for preventing parenteral abuse is also the dosage form of a multi-layer tablet disclosed in U.S. Pat. No. 6,309,668 (=WO 95/20947) which has the active substance with a potential for abuse and at least one gel former respectively separated in different layers.

A further approach for preventing parenteral abuse is disclosed in U.S. Pat. No. 7,214,385 (=WO 03/015531). This document describes a dosage form containing an analgesic opioid and a dye as an aversive agent. The color, released by inadmissible manipulation of the dosage form, is supposed to prevent the abuser from using this manipulated dosage form.

Another known possibility for impeding abuse is to add to the dosage form antagonists of the active substance, for example naloxone or naltrexone in the case of opioids, or to add to the dosage form compounds which lead to physiological deterrent reactions, for example Radix Ipecacuanha=ipecac root.

It is also known to prevent abuse by complicating or preventing the pulverization, necessary for abuse, of the dosage forms by the means usually available to a potential abuser. US 2005/031546 (=DE 103 36 400) discloses appropriately solid dosage forms containing active substance with abuse potential which, when used as intended, ensure the desired therapeutic effect, but from which the active substances cannot be converted by simple pulverization into a form capable of being abused.

These dosage forms secured against abuse are distinguished by a controlled, preferably retarded release of the active substance which has abuse potential. However, a rapid release of the active substance is necessary for numerous therapeutic applications, for example pain relief using active substances with abuse potential.

SUMMARY OF THE INVENTION

It was therefore the object of the present invention to provide a dosage form containing an active substance with abuse potential, the abuse of which is at least impeded and which dosage form ensures a reproducible, rapid release of the active substance with abuse potential.

This object is achieved by providing the multiparticulate dosage form according to the invention with impeded abuse potential, comprising
  at least one active substance with abuse potential (A),
  at least one synthetic or natural polymer (C),
  optionally at least one synthetic, semi-synthetic or natural wax (D),
  at least one disintegrating agent (E), and
  optionally one or more other physiologically acceptable auxiliaries (B),
the individual particles of the dosage form having a breaking strength of at least 500 N and an active substance release of at least 75% after 45 minutes, measured according to Pharm. Eur. in a paddle mixer with sinker in 600 ml of aqueous buffer solution with a pH value of 1.2 at 37° C. and 75 rpm (revolutions per minute).

By using polymers which have a minimum breaking strength of at least 500 N (measured as stated in the application) in quantities such that the particles of the dosage form according to the invention have a minimum breaking strength of at least 500 N it is possible to prevent pulverization of the dosage with usual means and thus prevent the subsequent abuse or to make it at least very difficult.

A parenteral, in particular an intravenous, safe application or an improper nasal application is impossible without an adequate comminution step, so that it is impossible to reach the intoxication-like, euphoric states achieved thereby in the desired intensity and with the desired rapidity.

According to the invention, the term comminution means the pulverization of the dosage form using conventional means usually available to an abuser, for example a pestle and mortar, a hammer, a mallet or other conventional means for pulverizing under the action of force.

The multiparticulate dosage forms according to the invention are therefore suitable for preventing the parenteral and/or nasal abuse of active substances, preferably pharmaceutical active substances, which have a potential for being misused and ensure a rapid, controlled release of the active substance due to their composition according to the invention. Therefore, they correspond to the so-called IR dosage forms (immediate release dosage forms), since the release profile of the active substance meets the corresponding standard conditions. The multiparticulate dosage forms most preferably exhibit a release of the active substances within 1 to 30 minutes.

Pharmaceutical active substances which have abuse potential are known to persons skilled in the art, as are the quantities thereof which are to be used and processes for the preparation thereof, and can be present as such in the dosage form according to the invention or, in the form of the corresponding derivatives thereof, in particular esters or ethers, or respectively in the form of corresponding physiologically acceptable compounds, in particular in the form of the corresponding salts or solvates thereof, as racemates or stereoisomers. The multiparticulate dosage form according to the invention is also suitable for the dosage of a plurality of pharmaceutical active substances in one dosage form. The dosage form preferably contains only one specific active ingredient with abuse potential.

The rapid release dosage form according to the invention is particularly suitable for impeding or preventing the abuse of at least one pharmaceutical active substance with abuse potential, selected from the group including opioids, tranquillisers, preferably benzodiazepine, barbiturates, stimulants and other narcotics, in particular active substances with a psychotropic effect.

The dosage form according to the invention is more particularly suitable for impeding or preventing the abuse of an opioid, a tranquillizer or another narcotic selected from the group consisting of N-{1-[2-(4-ethyl-5-oxo-2-tetrazolin-1-yl)ethyl]-4-methoxymethyl-4-piperidyl}propionanilide (alfentanil), 5,5-diallylbarbituric acid (allobarbital), allylprodine, alphaprodine, 8-chloro-1-methyl-6-phenyl-4H-[1,2,4]triazolo[4,3-a][1,4]-benzodiazepine (alprazolam), 2-diethylaminopropiophenone (amfepramone), (±)-α-methylphenethylamine (amphetamine), 2-α-methylphenethylamino)-2-phenylacetonitrile (amphetaminil), 5-ethyl-5-isopentylbarbituric acid (amobarbital), anileridine, apocodeine, 5,5-diethylbarbituric acid (barbital), benzylmorphine, beziramide, 7-bromo-5-(2-pyridyl)-1H-1,4-benzodiazepin-2(3H)-one (bromazepam), 2-bromo-4-(2-chlorophenyl)-9-methyl-6H-thieno[3,2-f][1,2,4]triazolo[4,3-a][1,4]diazepine (brotizolam), 17-cyclopropylmethyl-4,5α-epopxy-7α[(S)-1-hydroxy-1,2,2-trimethyl-propyl]-6-methoxy-6,14-endo-ethanomorphinan-3-ol (buprenorphine), 5-butyl-5-ethylbarbituric acid (butobarbital), butorphanol, (7-chloro-1,3-dihydro-1-methyl-2-oxo-5-phenyl-2H-1,4-benzodiazepin-3-yl)-dimethyl-carbamate (camazepam), (1S,2S)-2-amino-1-phenyl-1-propanol (cathine/D-norpseudoephedrine), 7-chloro-N-methyl-5-phenyl-3H-1,4-benzodiazepin-2-ylamine-4-oxide (chlorodiazepoxide), 7-chloro-1-methyl-5-phenyl-1H-1,5-benzodiazepine-2,4(3H,5H)-dione (clobazam), 5-(2-chlorophenyl)-7-nitro-1H-1,4-benzodiazepin-2(3H)-one (clonazepam), clonitazene, 7-chloro-2,3-dihydro-2-oxo-5-phenyl-1H-1,4-benzodiazepine-3-carboxylic acid (clorazepate), 5-(2-chlorophenyl)-7-ethyl-1-methyl-1H-thieno[2,3-e][1,4]diazepin-2(3H)-one (clotiazepam), 10-chloro-11b-(2chlorophenyl)-2,3,7,11b-tetrahydrooxazolo[3,2-d][1,4]benzodiazepine-6(5H)-one (cloxazolam), (−)-methyl-[3μ-benzoyloxy-2β(1αH,5αH)-tropancarboxylate] (cocaine), 4,5α-epoxy-3-methoxy-17-methyl-7-morphinen-6α-ol (codeine), 5-(1-cyclohexenyl)-5-ethylbarbituric acid (cyclobarbital), cyclorphan, cyprenorphine, 7-chloro-5-(2-chlorophenyl)-1H-1,4-benzodiazepin-2(3H)-one (delorazepam), desomorphine, dextromoramide, (+)-(1-benzyl-3-dimethylamino-2-methyl-1-phenylpropyl)propionate (dextropropoxyphene), dezocine, diampromide, diamorphone, diamorphine (heroin), 7-chloro-1-methyl-5-phenyl-1H-1,4-benzodiazepin-2(3H)-one (diazepam), 4,5α-epoxy-3-methoxy-17-methyl-6α-morphinanol (dihydrocodeine), 4,5α-epoxy-17-methyl-3,6α-morphinandiol (dihydromorphine), dimenoxadol, dimephetamol, dimethylthiambutene, dioxaphetylbutyrate, dipipanone, (6aR,10aR)-6,6,9-trimethyl-3-pentyl-6a,7,8,10a-tetrahydro-6H-benzo[c]chromen-1-ol (dronabinol), eptazocine, 8-chloro-6-phenyl-4H-[1,2,4]triazolo[4,3-a][1,4]benzodiazepine (estazolam), ethoheptazine, ethylmethylthiambutene, ethyl-[7-chloro-5-(2-fluorophenyl)-2,3-dihydro-2-oxo-1H-1,4 benzodiazepine-3-carboxylate] (ethylloflazepate), 4,5α-epoxy-3-ethoxy-17-methyl-7-morphinen-6α-ol (ethyl morphine), etonitazene, 4,5α-epoxy-7α-(1-hydroxy-1-methylbutyl)-6-methoxy-17-methyl-6,14-endo-etheno-morphinan-3-ol (etorphine), N-ethyl-3-phenyl-8,9,10-trinorbornan-2-ylamine (fencamfamine), 7-[2-(α-methylphenethylamino)ethyl]-theophylline) (fenetylline), 3-α-methylphenethylamino)propionitrile (fenproporex), N-(1-phenethyl-4-piperidyl)propionanilide (fentanyl), 7-chloro-5-(2-fluorophenyl)-1-methyl-1H-1,4-benzodiazepin-2(3H)-one (fludiazepam), 5-(2-fluorophenyl)-1-methyl-7-nitro-1H-1,4-benzodiazepin-2(3H)-one (flunitrazepam), 7-chloro-1-(2-diethylaminoethyl)-5-(2-fluorophenyl)-1H-1,4-benzodiazepin-2(3H)-one (flurazepam), 7-chloro-5-phenyl-1-(2,2,2-trifluoroethyl)-1H-1,4-benzodiazepin-2(3H)-one (halazepam), 10-bromo-11b-(2-fluorophenyl)-2,3,7,11b-tetrahydro[1,3]oxazolo[3,2-d][1,4]benzodiazepin-6(5H)-one (haloxazolam), heroin, 4,5α-epoxy-3-methoxy-17-methyl-6-morphinanone (hydrocodone), 4,5α-epoxy-3-hydroxy-17-methyl-6-morphinanone (hydromorphone), hydroxypethidine, isomethadone, hydroxymethylmorphinane, 11-chloro-8,12b-dihydro-2,8-dimethyl-12b-phenyl-4H-[1,3]oxazino[3,2-d][1,4]benzodiazepin-4,7(6H)-dione (ketazolam), 1-[4-(3-hydroxyphenyl)-1-methyl-4-piperidyl]-1-propanone (ketobemidone), (3S,6S)-6-dimethylamino-4,4-diphenylheptan-3-ylacetate (levacetylmethadol (LAAM)), (−)-6-dimethylamino-4,4-diphenyl-3-heptanone (levomethadone), (−)-17-methyl-3-morphinanol (levorphanol), levophenacylmorphane, lofentanil, 6-(2-chlorophenyl)-2-(4-methyl-1-piperazinylmethylene)-8-nitro-2H-imidazo[1,2-a][1,4]benzodiazepin-1(4H)-one (loprazolam), 7-chloro-5-(2-chlorophenyl)-3-hydroxy-1H-1,4-benzodiazepin-2(3H)-one (lorazepam), 7-chloro-5-(2-chlorophenyl)-3-hydroxy-1-methyl-1H-1,4-benzodiazepin-2(3H)-one (lormetazepam), 5-(4-chlorophenyl)-2,5-dihydro-3H-imidazo[2,1-a]isoindol-5-ol (mazindol), 7-chloro-2,3-dihydro-1-methyl-5-phenyl-1H-1,4-benzodiazepine (medazepam), N-(3-chloropropyl)-α-methylphenethylamine (mefenorex), meperidine, 2-methyl-2-propyltrimethylenedicarbamate (meprobamate), meptazinol, metazocine, methylmorphine, N,α-dimethylphenethylamine (methamphetamine), (+)-6-dimethylamino-4,4-diphenyl-3-heptanone (methadone), 2-methyl-3-o-tolyl-4(3H)-quinazolinone (methaqualone), methyl-[2-phenyl-2-(2-piperidyl)acetate] (methylphenidate), 5-ethyl-1-methyl-5-phenylbarbituric acid (methylphenobarbital), 3,3-diethyl-5-methyl-2,4-piperidindione (methyprylon), metopon, 8-chloro-6-(2-fluorophenyl)-1-methyl-4H-imidazo[1,5-a][1,4]benzodiazepine (midazolam), 2-(benzhydrylsulfinyl)acetamide (modafinil), 4,5α-epoxy-17-methyl-7-morphinene-3,6α-diol (morphine), myrophine, (±)-trans-3-(1,1-dimethylheptyl)-7,8,10,10α-tetrahydro-1-hydroxy-6,6-dimethyl-6H-dibenzo[b,d]pyran-9(6αH)-one (nabilone), nalbuphene, nalorphine, narceine, nicomorphine, 1-methyl-7-nitro-5-phenyl-1H-1,4-benzodiazepin-2(3H)-one (nimetazepam), 7-nitro-5-phenyl-1H-1,4-benzodiazepin-2(3H)-one (nitrazepam), 7-chloro-5-phenyl-1H-1,4-benzodiazepin-2(3H)-one (nordazepam), norlevorphanol, 6-dimethylamino-4,4-diphenyl-3-hexanone (normethadone), normorphine, norpipanone, the exudation of plants belonging to the species *Papaver somniferum* (opium), 7-chloro-3-hydroxy-5-phenyl-1H-1,4-benzodiazepine-2(3H)-one (oxazepam), (cis-trans)-10-chloro-2,3,7,11b-tetrahydro-2-methyl-11b-phenyloxazolo[3,2-d][1,4]benzodiazepin-6-(5H)-one (oxazolam), 4,5α-epoxy-14-hydroxy-3-methoxy-17-methyl-6-morphinanone (oxycodone), oxymorphone, plants and parts of plants belonging to the species *Papaver somniferum* (including the subspecies *setigerum*) (*Papaver somniferum*), papavereturn, 2-imino-5-phenyl-4-oxazolidinone (pernoline), 1,2,3,4,5,6-hexahydro-6,11-dimethyl-3-(3-methyl-2-butenyl)-2,6-methano-3-benzazocin-8-ol (pentazocine), 5-ethyl-5-(1-methylbutyl)-barbituric acid (pentobarbital), ethyl-(1-methyl-4-phenyl-4-piperidinecarboxylate) (pethidine), phenadoxone, phenomorphan, phenazocine, phenoperidine, piminodine, pholcodeine, 3-methyl-2-phenylmorpholine (phenmetrazine), 5-ethyl-5-phenylbarbituric acid (phenobarbital), α,α-dimethylphenethylamine (phentermine), 7-chloro-5-phenyl-1-(2-propinyl)-1H-1,4-benzodiazepin-2(3H)-one (pinazepam), α-(2-piperidyl)benzhydrylalcohol (pipradrol), 1'-(3-cyano-3,3-diphenylpropyl)[1,4'-bipiperidine]-4'-carboxamide (piritramide), 7-chloro-1-(cyclopropylmethyl)-5-phenyl-1H-1,4-benzodiazepin-2 (3H)-one (prazepam), profadol, proheptazine, promedol, properidine, propoxyphene, pseudoephedrine, N-(1-methyl-2-piperidinoethyl)-N-(2-pyridyl)propionamide, methyl{3-[4-methoxycarbonyl-4-(N-phenylpropanamido)piperidino] propanoate} (remifentanile), 5-sec-butyl-5-ethylbarbituric acid (secbutabarbital), 5-allyl-5-(1-methylbutyl)-barbituric acid (secobarbital), N-{4-methoxymethyl-1-[2-(2-thienyl) ethyl]-4-piperidyl}propionanilide (sufentanil), 7-chloro-2-hydroxy-methyl-5-phenyl-1H-1,4-benzodiazepin-2(3H)-one (temazepam), 7-chloro-5-(1-cyclohexenyl)-1-methyl-1H-1,4-benzodiazepin-2(3H)-one (tetrazepam), ethyl-(2-dimethylamino-1-phenyl-3-cyclohexene-1-carboxylate) (tilidine (cis and trans)), tramadol, 8-chloro-6-(2-chlorophenyl)-1-methyl-4H-[1,2,4]triazolo[4,3-a][1,4]benzodiazepine (triazolam), 5-(1-methylbutyl)-5-vinylbarbituric acid (vinylbital), (1R,2R)-3-(3-dimethylamino-1-ethyl-2-methyl-propyl)-phenol, (1R,2R,4S)-2-[dimethylamino)methyl-4-(p-fluorobenzyloxy)-1-(m-methoxyphenyl)cyclohexanol, (1R, 2R)-3-(2-dimethylaminomethyl-cyclohexyl)-phenol, (1S, 2S)-3(3-dimethylamino-1-ethyl-2-methyl-propyl)-phenol, (2R,3R)-1-dimethylamino-3(3-methoxy-phenyl)-2-methyl-pentan-3-ol, (1RS,3RS,6RS)-6-dimethylaminomethyl-1-(3-methoxy-phenyl)-cyclohexane-1,3-diol, preferably as racemate, 3-(2-dimethylaminomethyl-1-hydroxy-cyclohexyl)-phenyl 2-(4-isobutyl-phenyl)-propionate, 3-(2-dimethylaminomethyl-1-hydroxy-cyclohexyl)phenyl 2-(6-methoxy-naphthalen-2-yl)-xpropionate, 3-(2-dimethylaminomethyl-cyclohex-1-enyl)-phenyl 2-(4-isobutyl-phenyl)-propionate, 3-(2-dimethylaminomethyl-cyclohex-1-enyl)-phenyl 2-(6-methoxy-naphthalen-2-yl)-propionate, (RR—SS)-2-acetoxy-4-trifluoromethyl-benzoic acid 3-(2-dimethylaminomethyl-1-hydroxy-cyclohexyl)-phenyl ester, (RR—SS)-2-hydroxy-4-trifluoromethyl-benzoic acid 3-(2-dimethylaminomethyl-1-hydroxy-cyclohexyl)-phenyl ester, (RR—SS)-4-chloro-2-hydroxy-benzoic acid 3-(2-dimethylaminomethyl-1-hydroxy-cyclohexyl)-phenyl ester, (RR—SS)-2-hydroxy-4-methyl-benzoic acid 3-(2-dimethylaminomethyl-1-hydroxy-cyclohexyl)-phenyl ester, (RR—SS)-2-hydroxy-4-methoxy-benzoic acid 3-(2-dimethylaminomethyl-1-hydroxy-cyclohexyl)-phenyl-ester, (RR—SS)-2-hydroxy-5-nitro-benzoic acid 3-(2-dimethylaminomethyl-1-hydroxy-cyclohexyl)-phenyl ester, (RR—SS)-2',4'-difluoro-3-hydroxy-biphenyl-4-carboxylic acid 3-(2-dimethylaminomethyl-1-hydroxy-cyclohexyl)-phenyl ester and corresponding stereoisomeric compounds, respectively the corresponding derivatives thereof, in particular amides, esters or ethers, and respectively the physiologically acceptable compounds thereof, in particular the salts and solvates thereof, more preferably hydrochlorides.

The dosage form according to the invention is particularly suitable for impeding or preventing the abuse of an opioid active ingredient selected from the group consisting of oxycodone, diamorphine, ethylmorphine, hydrocodone, oxymorphone, hydromorphone, morphine, tramadol and the physiologically acceptable derivatives thereof or compounds, preferably the salts and solvates thereof, preferably the hydrochlorides thereof, physiologically acceptable enantiomers, stereoisomers, diastereomers and racemates and the physiologically acceptable derivatives thereof, preferably ethers, esters or amides.

Furthermore, the dosage form according to the invention is particularly suitable for impeding or preventing the abuse of an opioid active substance selected from the group consisting of (1R,2R)-3-(3-dimethylamino-1-ethyl-2-methyl-propyl)-phenol, (2R,3R)-1-dimethylamino-3-(3-methoxy-phenyl)-2-methyl-pentan-3-ol, (1RS,3RS,6RS)-6-dimethylaminomethyl-1-(3-methoxy-phenyl)-cyclohexane-1,3-diol, (1R,2R)-3-(2-dimethylaminonethyl-cyclohexyl)-phenol, the physiologically acceptable salts thereof, preferably hydrochlorides, phosphates, maleates, physiologically acceptable enantiomers, stereoisomers, diastereomers and racemates and the physiologically acceptable derivatives thereof, preferably ethers, esters or amides.

These compounds and respectively the preparation method thereof are described respectively in U.S. Pat. No. 6,248,737 (=EP 693,475) and U.S. Pat. No. 5,801,201 (=EP 780,369), the entire disclosures of which are incorporated herein by reference.

To achieve the requisite breaking strength of the particles of the dosage form according to the invention, at least one synthetic or natural polymer (C) is used which has a breaking strength, measured by the method disclosed in the present application, of at least 500 N. For this purpose, it is preferable to use at least one polymer selected from the group consisting of polyalkylene oxides, preferably polymethylene oxide, polyethylene oxide, polypropylene oxide; polyethylenes, polypropylenes, polyvinylchlorides, polycarbonates, polystyrenes, polyacrylates, the copolymers thereof and mixtures of at least two of the mentioned polymers. High-molecular-weight, thermoplastic polyalkylene oxides are particularly preferred. More preferred are high-molecular-weight polyethylene oxides having a molecular weight of at least 0.5 million, preferably of at least 1 million, more preferably 1 million to 15 million, most preferably from 1 to 10 million, determined by rheological measurements. These polymers have a viscosity at 25° C. of 4500 to 17600 cP, measured on a 5% by weight aqueous solution using a Brookfield viscosimeter, model RVF (spindle no. 2/rotation speed 2 rpm), of 400 to 4000 cP, measured on a 2% by weight aqueous solution using the mentioned viscosimeter (spindle no. 1 or 3/rotation speed 10 rpm) or a viscosity of 1650 to 10000 cP, measured on a 1% by weight aqueous solution using the mentioned viscosimeter (spindle no. 2/rotation speed 2 rpm). The polymers are preferably used as a powder. They can be soluble in water.

Furthermore, additionally to the polymer (C) to achieve the requisite breaking strength of the particles of the dosage form according to the invention, it is also possible to use at least one natural, semi-synthetic or synthetic wax (D) with a breaking strength, measured by the method disclosed in the present application, of at least 500 N. Waxes with a softening point of at least 50° C., more preferably 60° C. are preferred. Carnauba wax and beeswax are particularly preferred, especially carnauba wax. Carnauba wax is a natural wax which is obtained from the leaves of the carnauba palm and has a softening point of at least 80° C. When the wax component is additionally used, it is added together with at least one polymer (C) in quantities such that the particles of the dosage form have a breaking strength of at least 500 N.

Component (C) is preferably used in a quantity of from 35 to 99.9% by weight, more preferably in a quantity of at least 40% by weight and most preferably in a quantity of from 40 to 70% by weight, based on the total weight of the dosage form.

Physiologically acceptable disintegrats agents, such as are used for the preparation of pharmaceutical dosage forms can be used as disintegrats (E). Preferred for use as disintegrat (E) is at least one disintegrat selected from the group consisting of crosslinked sodium carboxymethyl cellulose (crosscamellose), modified maize starch, sodium carboxymethyl starch, crosslinked polyvinylpyrrolidone (crosspovidone). The dosage forms according to the invention preferably contain from 0.5 to 25% by weight, more preferably from 1 to 10% by weight, based on the total weight of the dosage form, of at least one disintegrating agent (E).

The disintegrat is preferably used in powder form and is present in the dosage form according to the invention in the particles and/or on the particles and/or distributed loosely alongside the particles. The disintegrating agent (E) is preferably at least partly in the form of a formulation component in the particles of the dosage form according to the invention and/or at least partly enveloping the particles, preferably in a coating on the particles and/or at least partly mixed with the particles of the dosage form. The disintegrat most preferably present as a formulation component in the particles and also as a component enveloping the particles.

The conventional auxiliaries (B1) which are preferably thermally stable and are known for the formulation of solid dosage forms can be used as further auxiliaries (B). These are preferably plasticizers, fillers, antioxidants and/or redox stabilizers.

Suitable antioxidants preferably include ascorbic acid, α-tocopherol, butylhydroxyanisol, butylhydroxytoluene, salts of ascorbic acid, ascorbylic palmitate, monothioglycerine, phosphoric acid, vitamin C, vitamin E and the derivatives thereof, such as vitamin E-succinate or vitamin E-palmitate and/or sodium bisulfite, more preferably butylhydroxytoluene (BHT) or butylhydroxyanisol (BHA) and/or α-tocopherol.

The antioxidant is preferably used in quantities of from 0.01 to 10% by weight, preferably from 0.03 to 5% by weight, based on the total weight of the dosage form.

Methylcellulose, hydroxyproplyl cellulose, hydroxyproplylmethyl cellulose, calcium dihydrogen phosphate and/or tricalcium phosphate can preferably also be used as fillers in the particles of the dosage form according to the invention.

Preferred plasticizers which may be used include polyalkylene glycols such as polyethylene glycol, fatty acids, fatty acid esters, waxes and/or microcrystalline waxes. The plasticizers are used preferably in a quantity of from 5 to 20% by weight, based on the total weight of the composition of the particles.

Preferably as redox stabilizers chelating agents like citric acid, EDTA (ethylenediaminetetra acetic acid), maleic acid and/or fumaric acid are used.

Fillers, taste improving additives and/or lubricants can also preferably be used as auxiliaries (B2), which preferably are not components of the particles.

Preferred fillers which may be used include microcrystalline cellulose, calciumdihydrogenphosphate, sugar like lactose, sugar alcohols like mannitol, hydroxyproplylmethyl cellulose, powder cellulose, collidone and/or polyvinylpyrrolidone.

As taste improving additives aroma additives, effervescent additives, sugar, sugar alcohols and/or sugar substitutes can be used preferably.

As lubricants talcum, silicon dioxide, stearic acid, fatty acid esters, sugar esters and/or magnesium stearate can be used.

The multiparticulate dosage forms according to the invention are characterized in that, due to their hardness, they cannot be pulverized by conventional crushing means available to an abuser, such as a pestle and mortar. This impedes or prevents a parenteral, in particular intravenous or nasal abuse. However, to prevent any possible abuse of the dosage forms according to the invention, in a preferred embodiment the dosage forms according to the invention can contain further abuse-impeding or abuse-preventing agents as auxiliaries (B3).

Thus, in addition to containing one or more active substance with abuse potential, at least one hardness-forming polymer (C), at least one disintegrat (E), optionally at least one wax (D), optionally other auxiliaries (B1, B2), the multiparticulate dosage forms according to the invention can also contain at least one of the following components (a)-(e) as auxiliaries (B3):
  (a) at least one substance which at least irritates the nasal cavity,
  (b) at least one antagonist for each of the active substances which are present in the dosage form and have abuse potential,
  (c) at least one emetic,
  (d) at least one dye as an aversive agent,
  (e) at least one bitter substance.

The components (a) to (e) are additionally each individually suitable for safeguarding the dosage form according to the invention against abuse. Thus, component (a) is preferably suitable for safeguarding against nasal and/or parenteral, preferably intravenous abuse, component (b) is preferably suitable for safeguarding against nasal and/or parenteral, more preferably intravenous abuse, component (c) is preferably suitable for safeguarding against parenteral, more preferably intravenous, and/or oral and/or nasal abuse, component (d) as a visual deterrent against oral or parenteral abuse and component (e) against oral or nasal abuse. The included use according to the invention of at least one of the aforementioned components makes it possible to impede abuse more effectively in the case of dosage forms according to the invention.

In one embodiment, the dosage form according to the invention can also contain one or more of the components (a)-(e) in a combination, preferably (a) and optionally (c) and/or (e) and/or (d) or (a) and optionally (c) and/or (d) and/or (e).

In a further embodiment, the dosage form according to the invention can contain all the components (a)-(e).

If the dosage form according to the invention comprises component (a) against abuse, substances considered according to the invention as irritating the nasal cavities and/or the pharynx are all those which, upon appropriate application via the nasal cavities and/or the pharynx, produce a reaction which is either so unpleasant for the abuser that he no longer wishes, or is able, to continue the application, for example a burning sensation, or which counteracts in a physiological manner the absorption of the corresponding active substance, for example by an increased nasal secretion production or by sneezing. These substances which usually irritate the nasal cavities and/or the pharynx can cause a very unpleasant feeling culminating in unbearable pain during parenteral, in particular intravenous application as well, so that the abuser no longer wishes, or is able, to continue administration.

Particularly suitable substances which irritate the nasal cavities and/or the pharynx are those which cause a burning sensation, an itching, an urge to sneeze, an increased secretion production or a combination of at least two of these stimuli. Appropriate substances and the quantities thereof which are conventionally to be used are known per se to a person skilled in the art or can be determined by simple preliminary tests.

The substance irritating the nasal cavities and/or pharynx of component (a) is preferably based on one or more constituents or one or more plant parts of at least one hot substance drug.

Suitable pungent drugs are known per se to persons skilled in the art and are described, for example in "Pharmazeutische Biologie—Drogen und ihre Inhaltsstoffe" (pharmaceutical biology—drugs and their ingredients) by Prof. Dr. Hildebert Wagner, $2^{nd}$ revised edition, Gustav Fischer Verlag, Stuttgart—New York, 1982, pages 82 ff, the disclosure of which is incorporated herein by reference.

A dosage unit of the multiparticulate dosage form according to the invention is understood as meaning a separate or separable dose, for example a capsule filling of the dosage form according to the invention.

It is possible to add to the dosage form according to the invention as component (a) preferably one or more constituents of at least one pungent drug selected from the group consisting of Allii sativi Bulbus, Asari Rhizoma c. Herba, Calami Rhizoma, Capsici Fructus (paprika), Capsici Fructus acer (cayenne pepper), Curcumae longae Rhizoma, Curcumae xanthorrhizae Rhizoma, Galangae Rhizoma, Myristicae Semen, Piperis nigri Fructus (pepper), Sinapis albae (Erucae) Semen, Sinapis nigri Semen, Zedoariae Rhizoma and Zingiberis Rhizoma, more preferably from the group consisting of Capsici Fructus (paprika), Capsici Fructus acer (cayenne pepper) and Piperis nigri Fructus (pepper).

The ingredients of the pungent drugs are preferably o-methoxy(methyl)-phenol compounds, acid amide compounds, mustard oils or sulfide compounds or compounds derived therefrom.

At least one ingredient of the pungent drugs is particularly preferably selected from the group consisting of myristicin, elemicin, isoeugenol, α-asaron, safrol, gingerols, xanthorrhizol, capsaicinoids, preferably capsaicin, capsaicin derivatives, such as N-vanillyl-9E-octadecenamide, dihydrocapsaicin, nordihydrocapsaicin, homocapsaicin, norcapsaicin, and nomorcapsaicin, piperine, preferably trans-piperine, glucosinolates, preferably based on non-volatile mustard oil, more preferably based on p-hydroxybenzyl mustard oil, methylmercapto mustard oil or methylsulfonyl mustard oil, and compounds derived from these ingredients.

The dosage form according to the invention can preferably contain the plant parts of the corresponding pungent drugs in a quantity of from 0.01 to 30% by weight, more preferably 0.1 to 0.5% by weight, in each case based on the total weight of a dosage unit or unit dose. If one or more ingredients of corresponding pungent drugs are used, they are used in a quantity of preferably 0.001 to 0.005% by weight, based on the total weight of the dosage unit or unit dose.

Furthermore, to prevent and safeguard against abuse, the dosage form according to the invention can contain the component (b), namely one or more antagonists for the active substance or the active substances with abuse potential, the quantity of antagonist preferably being spatially separated from the remaining ingredients of the dosage form according to the invention and not having any effect when used as intended.

Suitable antagonists for preventing misuse of the active substances are known per se to persons skilled in the art and can be present in the dosage form according to the invention as such or in the form of corresponding derivatives, in particular esters or ethers, or respectively in the form of corresponding physiologically acceptable compounds, in particular in the form of the salts or solvates thereof.

If the active substance present in the dosage form is an opioid, the antagonist which is used is preferably selected from the group consisting of naloxone, naltrexone, nalmefene, nalide, nalmexone, nalorphine or naluphine, in each case optionally in the form of a corresponding physiologically acceptable compound, in particular in the form of a base, a salt or solvate. The corresponding antagonists, where component (b) is provided, are preferably used in a quantity of ≥1 mg, more preferably in a quantity of from 3 to 100 mg, most preferably in a quantity of from 5 to 50 mg per dosage form, i.e. per unit dose.

If the dosage form according to the invention contains a stimulant as active substance, the antagonist is preferably a neuroleptic, preferably at least one compound selected from the group consisting of haloperidol, promethacine, fluphenazine, perphenazine, levomepromazine, thioridazine, perazine, chlorpromazine, chlorprothixine, zuclopentixol, flupentexol, prothipendyl, zotepin, benperidol, pipamperone, melperone and bromperidol.

The dosage form according to the invention preferably contains these antagonists in a conventional therapeutic dosage known to a person skilled in the art, more preferably in a quantity per unit dose which is double to three times the conventional dosage.

If the combination for preventing and safeguarding against abuse of the dosage form according to the invention comprises component (c), it can comprise at least one emetic which should preferably be in a spatially separated arrangement from the remaining components of the dosage form according to the invention and should not have any effect in the body when used as intended.

Suitable emetics for preventing abuse of an active ingredient are known per se to persons skilled in the art and can be present as such in the dosage form according to the invention, or in the form of corresponding derivatives, in particular esters or ethers, or respectively in the form of the respective corresponding physiologically acceptable compounds, in particular in the form of the salts or solvates thereof.

In the dosage form according to the invention, an emetic can be considered which is based on one or more constituents of Radix Ipecacuanhae (ipecac root), preferably based on the constituent emetine, as described, for example in "Pharmazeutische Biologie—Drogen und ihre Inhaltsstoffe" by Prof. Dr. Hildebert Wagner, $2^{nd}$ revised edition, Gustav Fischer Verlag, Stuttgart, New York, 1982, which is hereby incorporated herein by reference.

The dosage form according to the invention can preferably contain as component (c) the emetic emetine, preferably in a quantity of ≥3 mg, more preferably ≥10 mg and most preferably in a quantity of ≥20 mg per dosage form, i.e. per unit dose.

Apomorphine can likewise be preferably used as an emetic in safeguarding, according to the invention, against abuse, preferably in a quantity of preferably ≥3 mg, more preferably ≥5 mg and most preferably ≥7 mg per unit dose.

If the dosage form according to the invention contains component (d) as a further auxiliary preventing abuse, by using a dye of this type, in particular during an attempt to extract the active substance for a parenteral, preferably intravenous application, an intensive coloring of a corresponding aqueous solution is produced, which can deter a potential abuser. This coloring can also prevent an oral abuse which usually starts with an aqueous extraction of the active ingredient. Suitable dyes and the quantities required for the necessary deterrent effect are disclosed in U.S. Pat. No. 7,214,385 (=WO 03/015531) the entire disclosure of which is incorporated herein by reference.

If the dosage form according to the invention contains component (e) as a further auxiliary preventing abuse, oral and/or nasal abuse is further prevented by this addition of at least one bitter substance due to the taste of the dosage form being impaired.

Suitable bitter substances as well as the effective quantities are mentioned in U.S. Pat. No. 7,141,250, the entire disclosure of which is incorporated herein by reference. Suitable bitter substances preferably include aromatic oils, preferably peppermint oil, eucalyptus oil, bitter almond oil, menthol, fruit aroma substances, preferably aroma substances of lemons, oranges, limes, grapefruit or mixtures thereof, and/or denatonium benzoate (Bitrex®). Denatonium benzoate is particularly preferred.

The solid dosage form according to the invention is suitable for oral administration.

The multiparticulate dosage form according to the invention can be prepared by various processes which will be described in detail in the following; the invention also relates to dosage forms which can be obtained according to one of these processes:

The process for the preparation of the dosage form according to the invention preferably comprises the following steps:
(a) mixing the components (A), optionally (B), (C), optionally (D) and optionally at least partly (E);
(b) optionally pre-forming the mixture obtained from step (a), preferably under the effect of heat and/or force on the mixture obtained from (a), the supplied amount of heat preferably not being enough to heat component (C) to its softening point;
(c) hardening the mixture under the effect of heat and force, it being possible for the heat to be supplied during and/or before the effect of force and the supplied amount of heat being sufficient to heat component (C) at least to its softening point;
(d) dividing the hardened mixture;
(e) optionally forming into the dosage form; and
(f) optionally coating with a coating containing component (E) and/or mixing with component (E) and optionally additives (B2).

The heat can be supplied directly or by using ultrasound. The action of force and/or the forming procedure of the dosage form can be carried out, for example using suitable extruders, in particular using twin-screw extruders (double roller extruders) or planetary roller extruders.

The following process variants are particularly preferred:
Process Variant 1:

In this embodiment, the dosage form according to the invention is preferably prepared using an extruder, by mixing preferably components (A), optionally (B), (C), the optionally present component (D) and optionally component (E) at least a portion of which is also used and, optionally after being granulated, the resultant mixture is formed to produce the dosage form by being subjected to force while being previously or simultaneously exposed to heat. An extruder is used for this heating procedure and the effect of force to produce the dosage form.

The components (A), optionally (B), (C), and optionally (D) are mixed in a mixer known to a person skilled in the art. The mixer can be, for example a roller mixer, a shaking mixer, a shearing mixer or a compulsory mixer. The action of force is applied until the dosage form has reached a breaking hardness of at least 500 N. Granulation can be effected by moist granulation or by melt granulation in known granulators.

This variant for the preparation of the dosage form according to the invention is more preferably carried out such that:
a) the components (A), optionally (B), (C), the optionally present component (D) and optionally at least a portion of (E) are mixed;
b) the resultant mixture is heated in the extruder at least to the softening point of component (C) and is extruded through the outlet opening of the extruder under the action of force; and
c) the extrudate, which is still plastic, is divided and is optionally formed into the multiparticulate dosage form and optionally mixed and/or enveloped with component (E).

The components can preferably also be mixed according to process step a) in the extruder.

Prior to mixing with the further components, component (C) and the optionally present component (D) are preferably provided according to the invention with an antioxidant. This can be carried out by mixing the two components (C) and the antioxidant, preferably in that the antioxidant is dissolved or suspended in a volatile solvent and this solution or suspension is mixed homogeneously with component (C) and the optionally present component (D) and the solvent is removed by drying, preferably in an inert gas atmosphere.

The preferably molten mixture which has been heated in the extruder to at least the softening point of component (C) is extruded out of the extruder through a nozzle which has at least one orifice. To carry out the process according to the invention, it is necessary to use suitable extruders, preferably screw extruders (roller extruders), extruders provided with twin screws (rollers) being particularly preferred. The screws preferably have eccentric nozzles and the extruder is preferably equipped with a displacer cone.

Extrusion is preferably carried out such that the expansion of the extrudates as a result of extrusion is at the most 50%, i.e. for example when an extrusion nozzle is used which has 1 mm orifices, the extrudates have a maximum diameter of 1.5 mm. The strand expansion is more preferably at most of 40%, even more preferably at most 35%, most preferably at most 30% and in particular at most 25%. It has surprisingly been found that when the extruded material is subjected to an excessive mechanical stress in the extruder, the strand expands to a considerable extent, resulting in undesirable non-uniformity of properties, in particular in the mechanical properties of the extrudate.

The extruder preferably has at least two temperature zones, in which case in the first zone which adjoins a feed and optionally mixing zone, the mixture is heated at least to the softening point of component (C).

After being heated at least to the softening point of component (C), the molten mixture is transported by the screws, is further homogenized, compressed or compacted such that it has a minimum pressure of 5 bar, preferably at least 10 bar immediately before being discharged from the extruder nozzle, and is extruded through the nozzle as an extrudate or extrudates, depending on the number of nozzle orifices. The nozzle preferably has a plurality of orifices. The nozzle geometry or the geometry of the orifices can be freely chosen. Thus, the nozzle or the orifices can have a circular, oblong or oval cross section, the circular cross section preferably having a diameter of from 0.1 mm to 5 mm. The nozzle or orifices preferably has/have a circular cross section. The barrel of the extruder used according to the invention can be heated or cooled. The corresponding temperature adjustment, i.e. heating or cooling, is based on the mixture to be extruded at least one average temperature (product temperature) corresponding to the softening temperature of component (C) and not exceeding temperature at which the physiologically active substance (A) being processed can be damaged. The temperature of the mixture to be extruded is preferably set below 180° C., preferably below 150° C., but at least at the softening temperature of component (C).

After the molten mixture has been extruded and after the extrudates have optionally been cooled, the extrudates are preferably divided. This is preferably carried out by cutting the extrudates using a revolving or rotating knife, a water-jet cutters, wires, blades or by laser cutters. A pelletizing step preferably follows division of the extrudates.

The action of force in the extruder on the at least plasticized mixture is adjusted by controlling the rotational speed of the feed device in the extruder and by the geometry thereof and by the dimensioning of the outlet such that the necessary pressure builds up in the extruder preferably before the actual extruding of the plasticated mixture. Using simple preliminary tests it is possible to establish the necessary extrusion parameters required for a particular composition in order to produce a dosage form which has a breaking strength of at least 500 N.

An example of a suitable extruder is a twin screw extruder from the company Leistritz (Nürnberg) of type ZSE 18 HP 40D, preferably with screws which are equipped with eccentric screw ends. A heatable nozzle plate with 8 orifices each having a diameter of 1.0 mm can be used as the nozzle. The extrusion parameters can be set, for example at the following values: screw speed: 150 rpm; throughput: 2 kg/h; product temperature: 60° C. to 140° C., preferably 80° C. to 140° C., more preferably 100° C. to 140° C. and most preferably 110° C. to 140° C. with corresponding barrel temperature.

Process Variant 2:

In this process variant for the production of the dosage form according to the invention. Energy is supplied via ultrasound.

First, a homogeneous mixture is prepared from at least component (A), component (C), optionally component (D) and optionally a portion of component (E). Additional auxiliaries (B1), for example fillers, plasticizers, lubricants or colorants, can also be incorporated in this mixture. A low-molecular polyethylene glycol is preferably used as plasticizer.

Mixing can be carried out using conventional mixers. For example, roller mixers, which are also known as tumbler, drum or rotary mixers, container mixers, barrel mixers (drum hoop mixers or tumbling mixers) or shaking mixers, shearing mixers, positive mixers, plough-share mixers, planetary kneader mixers, Z-kneaders, sigma-kneaders, fluid mixers or intensive mixers are suitable as mixers. The choice of a suitable mixer depends among other things on the flowability and cohesive forces of the product.

The mixture then undergoes forming. Forming of the mixture is preferably carried out during or after sonication, e.g. exposure to ultrasound. During sonication it is especially preferable to have direct contact between the mixture and the sonotrode of the ultrasonic equipment. A frequency of 1 kHz to 2 MHz, preferably 15 to 40 kHz, should be maintained during sonication. Sonication should continue until softening of the polymer (C) is achieved. Preferably this is achieved within a few seconds, especially preferably within 0.1 to 5 seconds, preferably 0.5 to 3 seconds.

Before the forming operation is carried out, the mixing operation can be followed by granulation of the mixture, after which the resultant granules are formed, by sonication and the action of force, to the dosage form, such as tablets.

Granulation can be carried out in the machines and apparatus known by a person skilled in the art. If granulation is carried out as wet granulation, water or aqueous solutions, e.g. ethanol/water or isopropanol/water, can be used as the granulation fluid.

The mixture or the granules produced therefrom can preferably also be submitted, for further forming, to melt extrusion, in which the mixture is melted by sonication and the action of force and is then extruded through nozzles. The extrudates thus obtained are then comminuted by means of known devices to the desired length. The comminuted product thus obtained can also optionally be pelletized, in order to obtain the multiparticulate dosage form according to the invention with a minimum breaking strength of 500 N. The particles are preferably also provided with any remaining amount of disintegrant and optionally additives (B2), before they are filled to a unit dose, e.g. in capsules, or are compressed to a tablet.

When using ultrasound, suitable parameters for plastication are: frequency 20 kHz; amplitude 50%. Furthermore, a force of 250 N should be applied. The action of ultrasound and force by means of the sonotrode can take for example 0.5 s, with the action of ultrasound and force preferably taking place simultaneously.

Process Variant 3:

In this process variant for the production of the multiparticulate dosage form according to the invention, components (A), (C), optionally (D), optionally at least one part of the disintegrant (E) and any auxiliaries (B1) that are present, such as antioxidants and plasticizers, are processed by means of a planetary roller extruder to the dosage form according to the invention.

Planetary roller extruders are known and are described in detail inter alia in the Handbuch der Kunststoff-Extrusionstechnik [Handbook of plastics extrusion technology] I (1989) "Principles" in Chapter 1.2 "Classification of extruders" pages 4-6, which are hereby incorporated herein by reference.

BRIEF DESCRIPTION OF THE DRAWINGS

The use of a planetary roller extruder for the production of the dosage form according to the invention is explained below, referring to FIGS. 1 and 2. These explanations are only provided as examples and do not restrict the scope of the invention.

DETAILED DESCRIPTION

Figure 1:
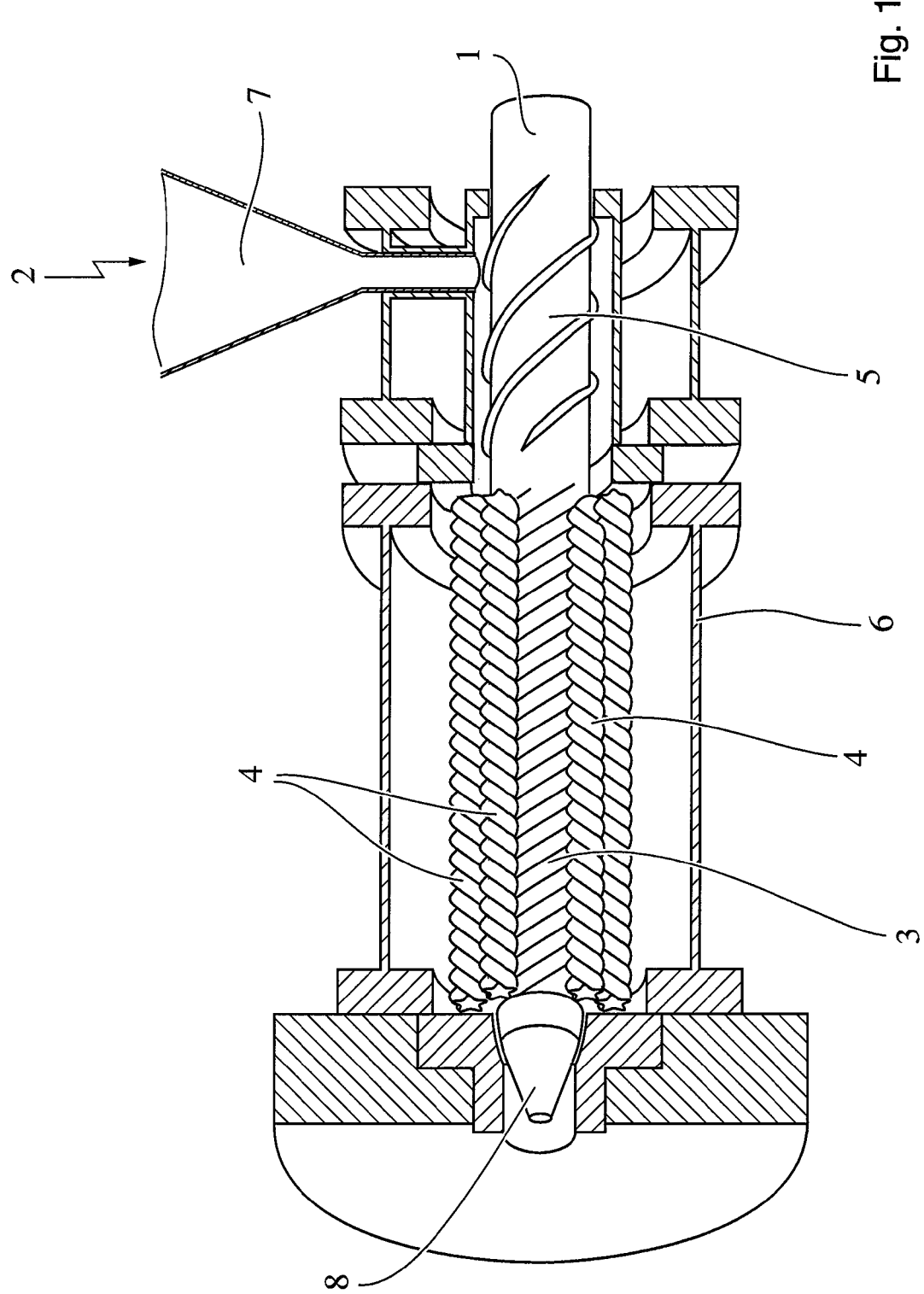
FIG. 1 shows a section through a planetary roller extruder.

FIG. 1 shows a planetary roller extruder, which can preferably be used for the production of the dosage forms according to the invention. This extruder essentially comprises a shaft 1, which, relative to the direction of feed of the mixture of the aforementioned components that is being extruded, is constituted first as feed screw 5 and thereafter as central spindle 3 of the planetary roller extruder. Around the central spindle 3 are arranged preferably three to seven planetary spindles 4, which are in their turn surrounded by a barrel in the form of a housing 6.

In the planetary roller extruder, referring to FIG. 1, the extrusion of the composition being used for production of a dosage form according to the invention is preferably carried out as follows. As indicated by arrow 2, the components to be extruded are fed through the metering unit 7 in the region of the feed screw 5 and are transported by the rotation (drive not shown) towards the central spindle 3. A person skilled in the art will understand that mixing together of the starting materials (components) is possible in the region of the feed screw. However, it is also possible to premix the components of the dosage form and feed this mixture via the metering unit 7 in the region of the feed screw 5. The mixture is transported in the feed section of the planetary roller extruder. By heating at least to the softening point of component (C), the mixture is melted and there, in the region of the central spindle, i.e. in the extrusion section, the molten mixture is transported by interaction of the central spindle 3 and of the planetary spindles 4, further homogenized, compressed or compacted and extruded as extrudates through the nozzle orifices 8. The nozzle geometry or the geometry of the orifices can be chosen freely. Thus, the orifices can have a circular, oblong or oval cross-section, and the circular cross-section preferably has a diameter of 0.1 mm to 5 mm. The orifices preferably have a circular cross-section. Both the barrel 6 of the planetary roller extruder that is used according to the invention and the central spindle can be heated or cooled. The corresponding temperature adjustment, i.e. heating or cooling, is based on the mixture to be extruded having at least an average temperature corresponding to the softening point of component (C) and not exceeding a temperature at which the substance (A) being processed can be damaged. Preferably the temperature of the mixture being extruded is below 180° C., preferably below 150° C., but is at least set to the softening point of component (C). The reference symbols used refer exclusively to FIGS. 1 and 2.

Extrusion of the molten mixture and optional cooling of the extrudates is followed by comminution of the extrudates (not shown in FIG. 1). The comminution can preferably be carried out by cutting of the extrudates by means of revolving or rotating knives, water-jet cutters, wires, blades or by means of laser cutters.

Optionally after further cooling of the comminuted extrudates, which are now preferably in the form of disks, optionally forming to the final form of the dosage form is carried out, preferably by pelletizing, and again with the action of heat if necessary.

The comminuted extrudates, optionally further formed, are preferably provided with (the remainder of) disintegrant (E) and optionally additives Finished in this way, as well as being compressed to tablets, they can also be used, in multiparticulate form, such as pellets or beads, for filling capsules, sachets, stick packs, in order to use the dosage form according to the invention as unit dose.

Figure 2:
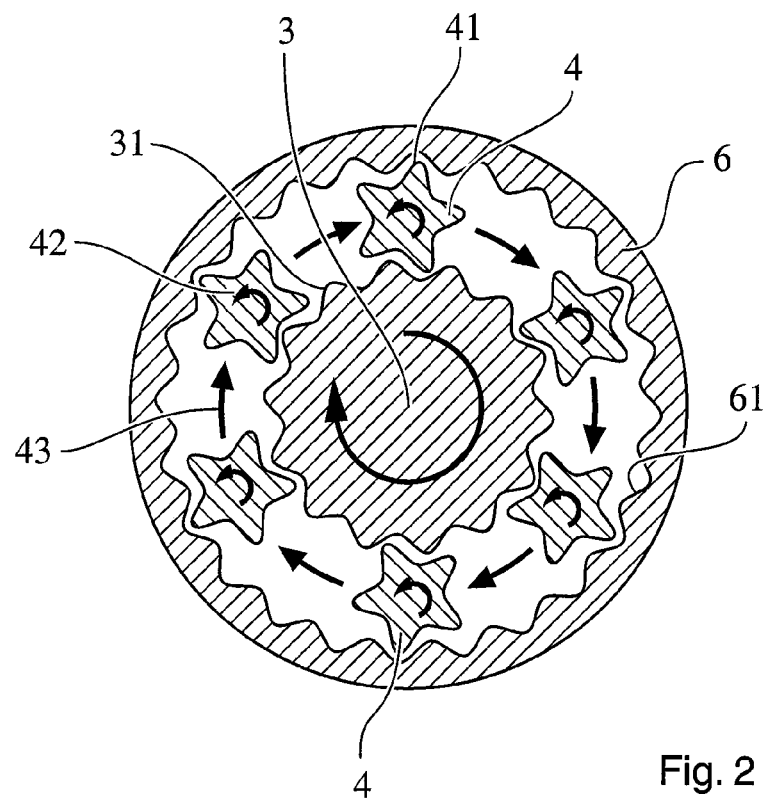
FIG. 2 shows the mode of action of the planetary roller extruder.

FIG. 2 shows a cross-section through the planetary roller extruder. Around the rotating central spindle 3, at least three, in the illustrated case shown 6, planetary spindles 4 are arranged, whose flanks 41 interact on the one hand with the flanks 31 of the central spindle 4 and on the other hand with the flanks 61 of the barrel 6 of the planetary roller extruder. Through the rotation of the central spindle 3 and the rolling of the respective flanks on one another, the planetary spindles 4 each rotate as shown by arrow 42 about their own axis and, as shown by arrow 43, about the central spindle 4. This leads to the desired compression or compacting of the mixture of components used according to the invention for the dosage forms produced according to the invention. The reference symbols used refer exclusively to FIGS. 1 and 2.

If necessary, the planetary roller extruder used can have not only an extrusion section, but also at least one other section, so that if required the mixture being extruded can also be degassed. The method can be carried out as a batch process or continuously, preferably continuously. A planetary roller extruder with four planetary spindles of type BCG 10 from the company LBB Bohle (Ennigerloh, Germany) with an extrusion nozzle with a diameter of 8 mm is, for example, suitable as the extruder. Gravity feed of 3.0 kg per hour is suitable. Extrusion can, for example, be carried out with a rotary speed of 28.6 rpm at a product temperature of approx. 88° C.

Process Variant 4:

In order to carry out this variant for the production of the dosage form according to the invention, at least the components (A), (C), optionally (D), optionally at least one part of the disintegrant (E) and any auxiliaries (B1) that are present, such as antioxidants and/or plasticizers, with addition of a solvent for component (C), i.e. for the polymer or polymers (C), are processed to the multiparticulate dosage form.

For this purpose, the components (A), optionally (B1), (C), component (D) if present and optionally at least one part of the disintegrant (E) are mixed together and the resultant formulation mixture, after addition of the solvent, is comminuted and optionally formed further.

The mixing of the components can be effected using mixers known to persons skilled in the art. The mixer can for example be a roller mixer, shaking mixer, shearing mixer or positive mixer.

The solvent for polymer (C) is added at least in amounts such that the formulation mixture is moistened uniformly. Preferably aqueous solvents, such as water, mixtures of water and aliphatic alcohols, preferably $C_1$-$C_6$ alcohols, esters, ethers, hydrocarbons, and especially preferably distilled water, short-chain alcohols, such as methanol, ethanol, isopropanol, butanol or aqueous alcoholic solutions, are suitable as the solvent for polymer (C). The solvent is preferably added while stirring. Then the uniformly moistened mass is dried, preferably after comminution. Drying is preferably carried out under the action of heat, at temperatures at which discoloration of the mass can be ruled out. This temperature can be determined by simple preliminary tests.

It is also possible in order to moisten the formulation mixture as follows: Before adding the solvent, the formulation mixture, preferably divided into part masses in forms, is dispersed in a liquid dispersant with stirring, and then the solvent is added. Component (C) is not soluble in the dispersant, which must be miscible with the solvent. Preferably hydrophilic solvents, such as aliphatic alcohols, ketones, and esters, are suitable as the dispersant. Short-chain alcohols are preferably used.

Alternatively, moistening of the formulation mixture can also be carried out by incorporating the solvent as foam in the formulation mixture. Preferably said solvent foam is produced using high-speed mixers, preferably with addition of usual foam stabilizers. Hydrophilic polymers, e.g. hydroxypropyl methylcellulose, are suitable for example as stabilizers. Preferably the foam is also incorporated in the formulation mixture with stirring, by which preferably a granulated mass is obtained.

The granulated mass is dried and is then formed to the multiparticulate dosage form, e.g. by pelletizing. Drying and forming can preferably be carried out as stated above. The method according to the invention can also be carried out by adding sufficient solvent to the formulation mixture to produce a formable paste.

The paste can be divided into partial masses before or after drying, which can be carried out as described above. The partial masses can be formed as strands, which can be produced by a sieve or an extruder. The dried strands are preferably comminuted and finally formed to the dosage form, e.g. by pelletizing. It is also possible to process the paste to a flat shape, and then stamp the dosage form from the dried shape. Advantageously, the paste is processed using an extruder, in which, depending on the form of extrusion, the strands or flat shapes are produced, and are comminuted by fragmenting or cutting or stamping. The comminuted partial masses can be formed or stamped as described above to the dosage form. Appropriate apparatus for this is known to persons skilled in the art.

In any case the finally formed, multiparticulate dosage forms are optionally further provided with the (remaining) amount of component (E) and optionally with additives (B2), before being filled or compressed as a unit dose. The method of solution according to the invention can be carried out as a continuous process or as a batch process.

It is also possible to add sufficient solvent to the formulation mixture so that at least the polymeric component (C) is dissolved. Said solution or dispersion/suspension is preferably processed to a flat shape, preferably using an extruder with a flat nozzle or pouring the solution onto a flat, smooth substrate.

After drying, as stated above, the multiparticulate dosage forms can be obtained from the flat shapes by stamping or calendering. It is also possible to process the solution, as stated above, to produce strands, which are then, preferably after drying, comminuted and formed to the dosage form.

Alternatively, the solution can also be divided into partial amounts such that, after drying, in each case they correspond to the mass of a unit of the dosage form, preferably already using forms corresponding to the shape of a unit of the dosage form. If the solution is divided into arbitrary partial amounts, the partial amounts can, after drying, optionally be combined again to a unit dose, which can for example be filled in a capsule or compressed to a tablet.

Preferably the formulation mixtures to which solvent has been added are processed at temperatures from 20° C. to 40° C., and apart from drying to remove the solvent and the dispersant that is optionally present, no higher temperatures are employed. The temperature for drying must be selected below the decomposition temperature of the components. Optionally, after forming to the dosage form, drying corresponding to that described above can also take place.

Combinations of individual process steps of the aforementioned variants of the method are also possible, for producing the dosage form according to the invention.

The multiparticulate dosage forms according to the invention are preferably provided with a coating of disintegrant (E), to provide IR-release of the active substance. It is at least advantageous to mix the particles, preferably pellets, of the dosage form according to the invention with a disintegrant (E) and to dilute the mixture preferably with additional filler (B2), such as microcrystalline cellulose, magnesium stearate, calcium dihydrogen phosphate, lactose, fatty acid esters, mannitol, hydroxypropyl methylcellulose, pulverized cellulose, talc, silica, collidon, sugar esters and/or polyvinyl pyrrolidone. Said mixtures can be filled as unit dose in capsules, sachets or stick packs or can be processed to chewable tablets, dispersible tablets or IR-tablets. Quite especially preferably, the particles or pellets of the dosage form according to the invention have a coating comprising at least one disintegrant (E), which was applied by powder coating or film coating. The stated unit doses can, depending on the intended use, additionally contain aromatic substances, effervescent additives, sugars, sweeteners and/or dyes.

If the dosage form according to the invention contains component (c) and/or (e), the dosage is to be selected so that with oral application as directed, no negative action is produced. If, however, the intended dosage is exceeded during misuse, this produces nausea or retching or a bad taste. The particular amount of component (c) and/or (e), that is still tolerated by the patient with oral application as directed, can be determined by a person skilled in the art by simple preliminary tests.

If, however, independently of the practically impossible pulverizability of the dosage form according to the invention for safeguarding the dosage form, the use of components (b) and/or (c) and/or (e) is envisaged, these components should preferably be used at such a high dosage that with misuse of the dosage form they cause an intensive negative action in the abuser. This is preferably achieved by spatial separation at least of the active substance or active substances from components (b) and/or (c) and/or (e), preferably with the active substance or active substances being present in at least one subunit (X) and the components (b) and/or (c) and/or (e) in at least one subunit (Y), and with the components (b), (e) with application of the dosage form as directed, they do not produce their action on ingestion and/or in the body and the other components of the formulation, in particular component (C) and optionally (D) and (E), are identical.

If the dosage form according to the invention has at least 2 of the components (b) and (c) or (e), these can in each case be contained in the same or in different subunits (Y). Preferably, if they are present, all components (b), (c) and (e) are contained in one and the same subunit (Y).

Subunits in the sense of the present invention are solid formulations, which in each case contain, apart from the usual excipients known by a person skilled in the art, the active substance(s), at least one polymer (C) and at least one disintegrant (E), component (D) if present and optionally at least one of the optionally present components (a) and/or (e) or in each case at least one polymer (C) and optionally (D) and at least one disintegrant (E) and the antagonist(s) and/or the emetic(s) and/or component (d) and/or component (e) and optionally at least one of the optionally present components (a). It should be noted that each of the stated subunits is formulated according to the method stated above.

A substantial advantage of separate formulation of the active substances from components (b) or (c) or (e) in subunits (X) and (Y) of the dosage form according to the invention is that with application as directed, components (b) and/or (c) and/or (e) are practically not released on ingestion and/or in the body, or are only released in such small amounts that they have no adverse effect on the patient or on the success of treatment, or on passage through the patient's body they are only released at locations where absorption is insufficient for them to have an effect. Preferably, with application of the dosage form as directed, components (b) and/or (c) and/or (e) are practically not released in the patient's body or are not noticed by the patient.

A person skilled in the art will understand that the aforesaid conditions can vary depending on the components (b), (c) and/or (e) used in each case and the formulation of the subunits or of the dosage form. The optimum formulation for a particular dosage form can be determined by simple preliminary tests. What is decisive is that the respective subunits contain the polymer (C), the disintegrant (E) and optionally the component (D) and were formulated in the manner presented above.

If, contrary to expectations, abusers succeed in comminuting said dosage form according to the invention, which has components (b), (c) and/or (e) in subunits (Y), for the purpose of abusive ingestion of the active substance, and in obtaining a powder that is extracted with a suitable extractant, then apart from the active substance, also the respective component (b), (c) and/or (e) is obtained in a form in which it cannot be separated easily from the active substance, so that on application of the manipulated dosage form, in particular with oral and/or parenteral administration, it exerts its action on ingestion and/or in the body and additionally one of the components (b) and/or (c) and/or (e) produces a corresponding negative action in the abuser or deters an attempt to extract the active substance because of the coloration and so prevents abuse of the dosage form.

The formulation of a dosage form according to the invention, in which spatial separation of the active substance or active substances from components (b), (c) and/or (e) is preferably effected by formulation in different subunits, can be carried out in a variety of ways, and the corresponding subunits in the dosage form according to the invention can in each case be in any spatial arrangement relative to one another, provided the aforesaid conditions for the release of components (b) and/or (c) and/or (e) are fulfilled.

A person skilled in the art will understand that the component(s) (a) that are also optionally present preferably both in the respective subunits (X) and (Y) and in the form of independent subunits corresponding to subunits (X) and (Y) can be formulated in the dosage form according to the invention, provided that protection of the dosage form against abuse as well as the release of active substance with application as directed are not adversely affected by the manner of formulation and polymer (C), the disintegrant (E) and optionally (D) are included in the formulation and formulation is carried out according to the methods stated above to achieve the necessary hardness.

In a preferred embodiment of the dosage form according to the invention, the two subunits (X) and (Y) are in multiparticulate form, with microtablets, granules, spheroids, beads or pellets being preferred, and the same form, i.e. shape is selected both for subunit (X) and for subunit (Y), so that separation of the subunits (X) from (Y), e.g. by mechanical sorting, is not possible. The multiparticulate forms preferably have a size in the range from 0.1 to 5 mm, preferably 0.2 to 3 mm.

The dosage form according to the invention is in multiparticulate form, preferably in the form of microtablets, granules, spheroids, beads or pellets, optionally filled as a unit dose in capsules or compressed to form tablets, for oral administration. Preferably the multiparticulate forms have a size in the range from 0.1 to 5 mm, especially preferably in the range from 0.2 to 3 mm (method of determination according to published dissertation "Systematic investigations of the suitability of kappa-carrageenan as pelletizing excipient in wet extrusion/spheroidization, pages 16, 21-23 by Markus Thommes in the "Deutsche Bibliothek" in the German National Bibliography, 1st edition Cuvillin Verlag, Göttingen, 2006).

The subunits (X) and (Y) in multiparticulate form can also preferably be filled in a capsule, sachets, stick packs or compressed to a tablet, with the subunits (X) and (Y) also being retained in the resultant unit doses.

The respective multiparticulate subunits (X) or (Y) with identical forming should also not be distinguishable from one another visually, so that they cannot be separated from one another by the abuser by simple sorting.

Preferably, release of components (b), (c) and/or (e) from subunit (Y) of the dosage form according to the invention is prevented by a coating, so that the subunit can consist of usual materials known by a person skilled in the art, provided it contains at least one polymer (C), and optionally (D) to fulfil the hardness condition of the dosage form according to the invention and is provided with disintegrant (E).

The materials listed below can preferably be used for coating. Examples of preferred materials include those selected from the group consisting of alkyl celluloses, hydroxyalkyl celluloses, glucans, scleroglucans, mannans, xanthans, copolymers of poly[bis(p-carboxyphenoxy)propane and sebacic acid, preferably at a molar ratio of 20:80 (marketed under the designation Polifeprosan 20®), carboxymethyl celluloses, cellulose ethers, cellulose esters, nitrocelluloses, polymers based on (meth)acrylic acid and esters thereof, polyamides, polycarbonates, polyalkylenes, polyalkylene glycols, polyalkylene oxides, polyalkylene terephthalates, polyvinyl alcohols, polyvinyl ethers, polyvinyl esters, halogenated polyvinyls, polyglycolides, polysiloxanes, polyurethanes, their copolymers and their mixtures.

Especially suitable materials can be selected from the group consisting of methylcellulose, ethylcellulose, hydroxypropylcellulose, hydroxypropyl methylcellulose, hydroxybutyl methylcellulose, cellulose acetate, cellulose propionate (of low, medium or increased molecular weight), cellulose acetate-propionate, cellulose acetate-butyrate, cellulose acetate-phthalate, carboxymethylcellulose, cellulose triacetate, sodium-cellulose sulfate, polymethylmethacrylate, polyethylmethacrylate, polybutylmethacrylate, polyisobutylmethacrylate, polyhexylmethacrylate, polyisodecylmethacrylate, polylaurylmethacrylate, polyphenylmethacrylate, polymethylacrylate, polyisopropylacrylate, polyisobutylacrylate, polyoctate-decylacrylate, polyethylene, low-density polyethylene, high-density polyethylene, polypropylene, polyethylene glycol, polyethylene oxide, polyethylene terephthalate, polyvinyl alcohol, polyvinyl isobutyl ether, polyvinyl acetate and polyvinyl chloride.

Especially suitable copolymers can be selected from the group consisting of copolymers of butylmethacrylate and isobutylmethacrylate, copolymers of methylvinylether and maleic acid with high molecular weight, copolymers of methylvinylether and maleic acid monoethyl ester, copolymers of methylvinylether and maleic acid anhydride and copolymers of vinyl alcohol and vinyl acetate.

Other materials especially suitable for formulation of a coating are starch-filled polycaprolactone, see U.S. Pat. No. 7,176,251 (=WO 98/20073), aliphatic polyester amides, see U.S. Pat. No. 6,344,535 (=DE 19 753 534), CA 2,317,747 (=DE 19 800 698), U.S. Pat. No. 5,928,739 (=EP 820,698), aliphatic and aromatic polyester urethanes, see U.S. Pat. No. 6,821,588 (=DE 198 22 979), polyhydroxyalkanoates, in particular polyhydroxybutyrates, polyhydroxyvalerates), casein, see U.S. Pat. No. 5,681,517 (=DE 4 309 528), polylactides and copolylactides, see U.S. Pat. No. 6,235,825 (=EP 980, 894). Each of the foregoing patent documents is hereby incorporated herein by reference in its entirety.

Optionally, the materials stated above can be mixed with other usual auxiliaries known by a person skilled in the art, preferably selected from the group consisting of plasticizers, lubricants, antioxidants, e.g. glycerol monostearate, semi-synthetic triglyceride derivatives, semi-synthetic glycerides, hydrogenated castor oil, glycerol palmitostearate, glycerol behenate, polyvinyl pyrrolidone, gelatin, magnesium stearate, stearic acid, sodium stearate, talc, sodium benzoate, boric acid and colloidal silica, fatty acids, substituted triglycerides, glycerides, polyoxyalkylene glycols, polyalkylene glycols and derivatives thereof.

The dosage form according to the invention displays IR-release, as defined above, of the active substance. It is therefore suitable preferably for treatment that is to have a quick effect, e.g. for control of acute pain.

Method of Determining the Breaking Strength

To verify whether a material can be used as component (C) or (D), the material is compressed to form a tablet with a diameter of 10 mm and a height of 5 mm with a force of 150 N, at a temperature corresponding at least to the softening point of the material and determined by means of a DSC diagram of the material. Tablets thus prepared are used for determining the breaking strength according to the method of determination of the breaking strength of tablets, published in the European Pharmacopoeia 1997, pages 143, 144, method No. 2.9.8., using the apparatus described below. The equipment used for the measurement is a Zwick material tester "Zwick Z 2.5", material tester Fmax 2.5 kN with a traverse of max. 1150 mm, which is to be adjusted by setting up by means of a column and a spindle, a rear clearance of 100 mm and a testing speed adjustable from 0.1 to 800 mm/min and test-Control software. A plunger die with screwable inserts and a cylinder (diameter 10 mm), a force transducer, Fmax. 1 kN, diameter 8 mm, class 0.5 from 10 N, class 1 from 2 N according to ISO 7500-1, with manufacturer's test certificate M according to DIN 55350-18 (Zwick-Bruttokraft Fmax 1.45 kN) are used for the measurement (all equipment from the company Zwick GmbH & Co. KG, Ulm, Germany) with Order No. BTC-FR 2.5 TH. D09 for the tester, Order No. BTC-LC 0050N. P01 for the force transducer, Order No. BO 70000 S06 for the centring device.

Figure 3:
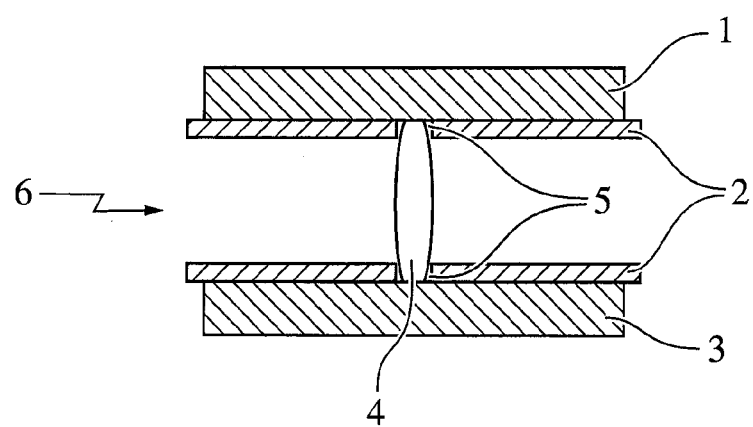
FIG. 3 shows the measurement of the breaking strength of a tablet.

FIG. 3 shows the measurement of the breaking strength of a tablet, in particular the adjuster (6) of the tablet (4) used before and during the measurement. For this, the tablet (4) is clamped between the upper pressure plate (1) and the lower pressure plate (3) of the device (not shown) for application of the force, by means of two 2-part clamping devices, which in each case are firmly secured (not shown) with the upper or lower pressure plate after setting the necessary distance (5) for receiving and for centring the tablet that is to be measured. For adjusting the distance (5), the 2-part clamping devices can in each case be moved horizontally outwards or inwards on the pressure plate carrying them.

Tablets for which no breakage was found, but possibly plastic deformation of the tablet without fracture occurred under the action of force, are also classed as breakage-resistant under the action of a defined force.

With the dosage forms obtained according to the invention, the breaking strength is determined by the method of measurement described, and the particles of the multiparticulate dosage forms other than tablets are also tested.

The invention will be explained in further detail hereinafter with reference to illustrative examples. These explanations are only provided as examples and do not limit the general scope of the invention.

EXAMPLES

Tramadol hydrochloride was used as the active substance in a number of examples. Tramadol hydrochloride was used, although tramadol is not an active substance with usual potential for misuse and therefore is not covered by the Narcotics Law, in order to facilitate the experimental work. Moreover, tramadol is a representative of the opioids class with excellent solubility in water.

Example 1

Pellet Production

Composition of the Pellets:

|  | | Proportion [%] |
|---|---|---|
| Tramadol HCl | 50 mg | 40% |
| Polyethylene oxide, NF 7 000 000 (MW) (Polyox WSR 303, Dow Chemicals) | 50 mg | 40% |
| (Metholose 90 SH, 100000 cP) hydroxypropyl methylcellulose (Shin-Etsu) | 12.5 mg | 10% |
| PEG 6000 (polyethylene glycol) | 12.5 mg | 10% |

The components were weighed and then mixed in a tumbler for 15 minutes. Then they were extruded using a twin-screw extruder from the company Leistritz, type ZSE18HP40D with micropelletizer. Eccentric screw tips and a displacer cone were used. The nozzle plate had eight orifices with a diameter of 1.0 mm and the length/diameter ratio was 2.5. The resultant pellets had a length of 1 mm±20%. The process parameters were as follows:

| Barrel temperature HZ1 required 40° C./actual: | 39.6° C. |
|---|---|
| Barrel temperature HZ2 and HZ2 | 100° C. |
| Barrel temperature HZ4 to HZ8 | 120° C. |
| Barrel temperature HZ10 | 120° C. |
| Barrel temperature HZ11 | 140° C. |
| Product temperature at discharge end | 134.1° C. |
| Discharge rate | 33.43 g/min |
| Screw speed (1/min) | 150/min |

The breaking strength of the pellets was determined by the method described above with the apparatus shown in FIG. 3. Fracture did not occur under the action of a force of 500 N. The pellets could not be crushed with a hammer, nor using pestle and mortar.

1.1. Capsule Production

Composition of the Capsule Filling

| Pellets produced according to Example 1.1. (≈50 mg tramadol) | 125 mg | 95% |
|---|---|---|
| Crospovidone | 6.3 mg | 5% |
| Total amount | 131.3 mg | 100% |

The pellets produced according to 1.1. were mixed with crospovidone until a homogeneous mixture was obtained. Gelatin two-piece capsules of size 0 were filled with this mixture.

The in-vitro release of tramadol from the capsule was determined according to Ph.Eur. in a paddle stirrer with sinker. The temperature of the release medium was 37° C. and the rotary speed of the stirrer was 75 min$^{-1}$. 600 ml of buffer pH 1.2 was used as the release medium. The amount of tramadol released in each case in the dissolution medium at a specified time was determined by spectrophotometry (at 271 nm).

| Time | Amount of active substance released |
| --- | --- |
| 15 min | 56% |
| 30 min | 80% |
| 45 min | 89% |

Example 2

2.1. Pellets Produced According to Example 1.1. Are Used 2.2. Composition of the Capsule Filling

| | | |
| --- | --- | --- |
| Pellets produced according to example 1.1. ($\cong$50 mg tramadol) | 125 mg | 95% |
| Croscarmellose | 6.3 mg | 5% |
| Total amount | 131.3 mg | 100% |

The pellets were mixed with croscarmellose and filled in gelatin two-piece capsules of size 0. The in-vitro release of tramadol from the capsule was determined according to Ph.Eur. in a paddle stirrer with sinker. The temperature of the release medium was 37° C. and the rotary speed of the stirrer was 75 $min^{-1}$. 600 ml of buffer pH 1.2 was used as the release medium. The amount of active substance released in each case in the dissolution medium at a specified time was determined by spectrophotometry (at 271 nm).

| Time | Amount of active substance released |
| --- | --- |
| 15 min | 44% |
| 30 min | 71% |
| 45 min | 82% |

Example 3

3.1. Pellets Produced According to Example 1.1. Are Used 3.2. Composition of the Capsule Filling

| | | |
| --- | --- | --- |
| Pellets produced according to Example 1.1. ($\cong$50 mg tramadol) | 125 mg | 73.8% |
| Crospovidone | 6.3 mg | 3.7% |
| Microcrystalline cellulose (Avicel PH101) | 37.5 mg | 22.1% |
| Magnesium stearate | 0.6 mg | 0.4% |
| Total amount | 169.4 mg | 100% |

The pellets were mixed with croscarmellose, microcrystalline cellulose and magnesium stearate and filled in gelatin two-piece capsules of size 0. The in-vitro release of tramadol from the capsule was determined according to Ph.Eur. in a paddle stirrer with sinker. The temperature of the release medium was 37° C. and the rotary speed of the stirrer was 75 $min^{-}$. 600 ml of buffer pH 1.2 was used as the release medium. The amount of active substance released in each case in the dissolution medium at a specified time was determined by spectrophotometry (at 271 nm).

| Time | Amount of active substance released |
| --- | --- |
| 15 min | 70% |
| 30 min | 88% |
| 45 min | 92% |

Example 4

4.1. Pellets Produced According to Example 1.1. Were Used 4.2. Composition of the Capsule Filling

| | | |
| --- | --- | --- |
| Pellets produced according to Example 1.1. ($\cong$50 mg tramadol) | 125 mg | 66.7% |
| Croscarmellose | 6.25 mg | 3.3% |
| Microcrystalline cellulose (Avicel PH101) | 50.0 mg | 26.7% |
| Calcium dihydrogen phosphate | 6.25 mg | 3.3% |
| Total amount | 187.5 mg | 100% |

The pellets were mixed with the excipients and filled in gelatin two-piece capsules of size 0. The in-vitro release of tramadol from the capsule was determined according to Ph.Eur. in a paddle stirrer with sinker. The temperature of the release medium was 37° C. and the rotary speed of the stirrer was 75 $min^{-}$. 600 ml of buffer pH 1.2 was used as the release medium. The amount of active substance released in each case in the dissolution medium at a specified time was determined by spectrophotometry (at 271 nm).

| Time | Amount of active substance released |
| --- | --- |
| 15 min | 51% |
| 30 min | 80% |
| 45 min | 88% |

Example 5

5.1. Pellets Produced According to Example 1.1. Were Used 5.2. Composition of the Capsule Filling

| | | |
| --- | --- | --- |
| Pellets produced according to Example 1.1. ($\cong$50 mg tramadol) | 125 mg | 95.2% |
| Crospovidone, micronized | 6.25 mg | 4.8% |
| Total amount | 131.25 mg | 100% |

Crospovidone (micronized) and pellets were mixed in a high-shear mixer (Diosna Laborgranulator 4) for 15 minutes. The coated pellets were filled in a gelatin capsule of size 0.

The breaking strength of the pellets was determined by the method described above, with the apparatus stated there. Breakage did not occur under the action of a force of 500 N. The pellets could not be crushed with a hammer, nor was this possible using a pestle and mortar.

The in-vitro release of tramadol from the capsule was determined according to Ph.Eur. in a paddle stirrer with sinker. The temperature of the release medium was 37° C. and the rotary speed of the stirrer was 75 $min^{-1}$. 600 ml of buffer pH 1.2 was used as the release medium. The amount of active substance released in each case in the dissolution medium at a specified time was determined by spectrophotometry (at 271 nm).

| Time | Amount of active substance released |
| --- | --- |
| 15 min | 52% |
| 30 min | 77% |
| 45 min | 86% |

Example 6

6.1. Pellet Production

Composition of the Pellets

| | Per capsule filling | Proportion [%] |
| --- | --- | --- |
| Tramadol HCl | 50 mg | 45% |
| Polyethylene oxide 7 000 000 (MW) (Polyox WSR 303, Dow Chemicals) | 44.4 mg | 40% |
| Macrogol 6000 (polyethylene glycol 6000 BASF) | 11.1 mg | 10% |
| Crospovidone | 5.6 mg | 5% |

The components were weighed and then mixed in a tumbler for 15 minutes. Then they were extruded by means of a twin-screw extruder from the company Leistritz, type ZSE18HP40D with micropelletizer. Eccentric screw tips and a displacer cone were used. The nozzle plate had eight orifices with a diameter of 1.0 mm, with length/diameter ratio of 2.5. Pellet length was 1 mm±20%. The extrusion parameters were as follows:

| Barrel temperature HZ1 required 40° C./actual: | 39.6° C. |
| --- | --- |
| Barrel temperature HZ2 and HZ2 | 100° C. |
| Barrel temperature HZ4 to HZ8 | 120° C. |
| Barrel temperature HZ10 | 120° C. |
| Barrel temperature HZ11 | 140° C. |
| Product temperature in discharge section | 134.1° C. |
| Discharge rate | 33.43 g/min |
| Screw speed (1/min) | 150/min |

The breaking strength of the pellets was determined by the method described above, with the apparatus stated there. Breakage did not occur under the action of a force of 500 N. The pellets could not be crushed with a hammer, nor was this possible using pestle and mortar.

6.2. Composition of the Capsule Filling

| Pellets produced according to Example 6.1. (≈50 mg tramadol) | 111 mg | 100% |
| --- | --- | --- |
| Total amount | 111 mg | 100% |

The pellets produced according to 6.1. were filled in gelatin two-piece capsules of size 0. The in-vitro release of tramadol from the capsule was determined according to Ph.Eur. in a paddle stirrer with sinker. The temperature of the release medium was 37° C. and the rotary speed of the stirrer was 75 $min^{-1}$. 600 ml of buffer pH 1.2 was used as the release medium. The amount of active substance released in each case in the dissolution medium at a specified time was determined by spectrophotometry (at 271 nm).

| Time | Amount of active substance released |
| --- | --- |
| 15 min | 55% |
| 30 min | 77% |
| 45 min | 87% |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents.

What is claimed is:

1. A multiparticulate dosage form with impeded abuse, comprising
    at least one active substance with abuse potential (A) having a psychotropic action and being selected from the group consisting of opioids,
    at least one synthetic or natural polymer (C),
    optionally at least one natural, semi-synthetic or synthetic wax (D),
    at least one disintegrant (E), which is selected from the group consisting of crosspovidone and crosscarmellose, wherein at least part of the disintegrant (E) is mixed with the particles of the dosage form,
    an auxiliary (B2), which is microcrystalline cellulose, and which is not a component of the particles,
    optionally one or more additional, physiologically acceptable auxiliaries,
    wherein the individual particles of the dosage form have a breaking strength of at least 500 N and a release of active substance of at least 75% after 45 minutes measured according to Ph.Eur. in a paddle mixer with sinker in 600 ml of aqueous buffer solution with a pH value of 1.2 at 37° C. and 75 revolutions per minute.

2. A dosage form according to claim 1, wherein said dosage form is in the form of microtablets, micropellets, granules, spheroids, beads or pellets.

3. A dosage form as claimed in claim 1 wherein said at least one polymer is selected from the group consisting of polyalkylene oxides, polyethylenes, polypropylenes, polyvinyl chlorides, polycarbonates, polystyrenes, polyacrylates and copolymers thereof.

4. A dosage form as claimed in claim 1, wherein said at least one polymer comprises a polyalkylene oxide selected from the group consisting of polymethylene oxides, polyethylene oxides, polypropylene oxides, copolymers of polyethylene oxide, copolymers of polypropylene oxide, block copolymers of polyethylene oxide, block copolymers of polypropylene oxide, and mixtures thereof said polyalkylene oxide having a molecular weight of at least $0.5 \times 10^6$ based on rheological measurements.

5. A dosage form as claimed in claim 3, wherein said polymer has a molecular weight of from $1 \times 10^6$ to $15 \times 10^6$ based on rheological measurements.

6. A dosage form as claimed in claim 1, wherein the wax is carnauba wax, beeswax, or a mixture of carnauba wax and beeswax, and said wax has a softening point of at least 50° C. and a breaking strength of at least 500 N.

7. A dosage form as claimed in claim 1, wherein said disintegrant is disposed in the particles, or on the particles, or loosely distributed among the particles, or two or more of the foregoing.

8. A dosage form as claimed in claim 7, wherein the disintegrant is at least partially present as a component in the particles.

9. A dosage form as claimed in claim 7, wherein the disintegrant is at least partially present in a coating enveloping the particles.

10. A dosage form as claimed in claim 7, wherein the disintegrant is admixed with particles of the dosage form.

11. A dosage form as claimed in claim 7, wherein the disintegrant is present both as a component in the particles and in a coating enveloping the particles.

12. A dosage form as claimed in claim 1, comprising from 0.1 to 15 wt. % of said disintegrant relative to the total weight of the dosage form.

13. A dosage form as claimed in claim 12, comprising from 3 to 7 wt. % of said disintegrant relative to the total weight of the dosage form.

14. A dosage form as claimed in claim 1, wherein said active substance with abuse potential is distributed in a matrix having a breaking strength of at least 500 N and comprising at least one polymer.

15. A dosage form as claimed in claim 14, wherein said matrix further comprises at least one wax, or at least one formulation auxiliary, or at least part of the disintegrant, or two or more of the foregoing.

16. A dosage form as claimed in claim 1, wherein the particles are compressed to tablets or chewable tablets or are filled in capsules, sachets or stick-packs.

17. A dosage form as claimed in claim 1, wherein the particles have a particle size in the range from 0.1 to 5 mm.

18. A dosage form as claimed in claim 17, wherein the particles have a diameter in the range from 0.2 to 3 mm.

19. A multiparticulate dosage form with impeded abuse comprising a mixture of the following distinct components:
(a) particles comprising:
(i) at least one active substance with abuse potential (A) having a psychotropic action and being selected from the group consisting of opioids;
(ii) optionally one or more additional, physiologically acceptable auxiliaries (B);
(iii) at least one synthetic or natural polymer (C); and
(iv) optionally at least one natural, semi-synthetic or synthetic wax (D);
(b) at least one disintegrant (E), which is selected from the group consisting of crosspovidone and crosscarmellose, said at least one disintegrant (E) being separate from the particles; and
(c) a filler (B2), which is microcrystalline cellulose, said filler (B2) also being separate from the particles;
wherein the particles have a breaking strength of at least 500 N and a release of active substance of at least 75% after 45 minutes measured according to Ph.Eur. in a paddle mixer with sinker in 600 ml of aqueous buffer solution with a pH value of 1.2 at 37° C. and 75 revolutions per minute.

20. The dosage form as claimed in claim 19, wherein the particles themselves comprise some content of disintegrant (E) and this content of disintegrant (E) is in addition to the disintegrant (E) kept separate from the particles.

21. A method of preparing a dosage form as claimed in claim 1, said method comprising: (a) mixing components (A), (C), optionally auxiliaries (B1) selected from the group consisting of fillers, plasticizers, lubricants and colorants, optionally (D) and optionally at least a portion of the disintegrant (E); (b) optionally preforming of the mixture obtained from step a) under the action of heat or force or both on the mixture obtained from a) without softening of component (C); (c) hardening of the mixture under the action of heat and force, wherein the heat is supplied during or before or both during and before the action of force and is sufficient to heat component (C) at least to its softening point; (d) dividing of the hardened mixture into partial masses; (e) dividing of the hardened partial masses and optionally forming; (f) enveloping, coating or mixing with the portion of disintegrant (E) remaining from a) and optionally additional auxiliaries (B2); and (g) optionally final forming or filling to a unit dose of the dosage form.

22. A method as claimed in claim 21, wherein a screw extruder or a planetary roller extruder is used at least in step c), and in step c), heat is supplied by exposure to ultrasound.

23. A dosage form obtained by the method of claim 21.

24. A method of preparing a dosage form as claimed in claim 1, said method comprising: mixing of components (A), (C), optionally auxiliaries (B1) selected from the group consisting of fillers, plasticizers, lubricants and colorants, optionally (D) and optionally at least one portion of disintegrant (E) with addition of a solvent for polymer (C) at least in amounts such that the mixture is simultaneously moistened and is deformable, dividing the formable mass into partial masses before or after drying, dividing the partial masses obtained, optionally after further distribution, and optionally forming, enveloping, coating or mixing the divided partial masses with the remainder of disintegrant (E) and optionally additional auxiliaries (B2), and optionally final forming or filling to a unit dose of the dosage form.

25. A dosage form obtainable by the method of claim 24.

\* \* \* \* \*

UNITED STATES PATENT AND TRADEMARK OFFICE
CERTIFICATE OF CORRECTION

PATENT NO.         : 8,722,086 B2                                   Page 1 of 1
APPLICATION NO.    : 12/044586
DATED              : May 13, 2014
INVENTOR(S)        : Arkenau-Marić et al.

It is certified that error appears in the above-identified patent and that said Letters Patent is hereby corrected as shown below:

In the specification

Column 3, line 58, "[3µ" -- should read -- [3β --.

Column 4, line 50, "(+)" -- should read -- (±) --.

Column 24, line 2, "min⁻" -- should read -- $min^{-1}$ --.

Column 24, line 39, "75 min⁻" -- should read -- $75\ min^{-1}$ --.

Signed and Sealed this
First Day of December, 2015

Michelle K. Lee
*Director of the United States Patent and Trademark Office*